United States Patent
Brigé et al.

(10) Patent No.: US 9,534,039 B2
(45) Date of Patent: Jan. 3, 2017

(54) METHOD FOR THE PRODUCTION OF IMMUNOGLOBULIN SINGLE VARIABLE DOMAINS

(75) Inventors: Ann Brigé, Ertvelde (BE); Peter Schotte, De Pinte (BE); Bart Walcarius, Gentbrugge (BE)

(73) Assignee: Ablynx N.V., Zwijinaarde (BE)

( * ) Notice: Subject to any disclaimer, the term of this patent is extended or adjusted under 35 U.S.C. 154(b) by 320 days.

(21) Appl. No.: 14/116,153

(22) PCT Filed: May 9, 2012

(86) PCT No.: PCT/EP2012/058525
§ 371 (c)(1),
(2), (4) Date: Feb. 4, 2014

(87) PCT Pub. No.: WO2012/152823
PCT Pub. Date: Nov. 15, 2012

(65) Prior Publication Data
US 2014/0141507 A1    May 22, 2014

Related U.S. Application Data

(60) Provisional application No. 61/484,109, filed on May 9, 2011.

(51) Int. Cl.
*C12P 21/02* (2006.01)
*C07K 16/00* (2006.01)
*C12N 15/81* (2006.01)

(52) U.S. Cl.
CPC ............ *C07K 16/00* (2013.01); *C12N 15/815* (2013.01); *C07K 2317/14* (2013.01); *C07K 2317/22* (2013.01); *C07K 2317/569* (2013.01); *C12P 21/02* (2013.01)

(58) Field of Classification Search
None
See application file for complete search history.

(56) References Cited

FOREIGN PATENT DOCUMENTS

| WO | WO 94/25591 A1 | 11/1994 |
|---|---|---|
| WO | WO 02/086101 A2 | 10/2002 |
| WO | WO 2007/148345 A2 | 12/2007 |
| WO | WO 2009/084841 A2 | 7/2009 |
| WO | WO 2010/125187 A2 | 11/2010 |
| WO | WO 2010/135678 A1 | 11/2010 |

OTHER PUBLICATIONS

De Schutter et al., Genome sequence of the recombinant protein production host Pichia pastoris. Nat Biotechnol. Jun. 2009;27(6):561-6. doi: 10.1038/nbt.1544. Epub May 24, 2009.
Eldin et al., High-level secretion of two antibody single chain Fv fragments by Pichia pastoris. J Immunol Methods. Feb. 14, 1997;201(1):67-75.
Esposito et al., Gateway cloning is compatible with protein secretion from Pichia pastoris. Protein Expr Purif. Apr. 2005;40(2):424-8.
Fuller et al., Enzymes required for yeast prohormone processing. Annu Rev Physiol. 1988;50:345-62.
Ghosalkar et al., Secretory expression of interferon-alpha 2b in recombinant Pichia pastoris using three different secretion signals. Protein Expr Purif. Aug. 2008;60(2):103-9. doi: 10.1016/j.pep.2008.02.006. Epub Feb. 29, 2008.
Kurjan et al., Structure of a yeast pheromone gene (MF alpha): a putative alpha-factor precursor contains four tandem copies of mature alpha-factor. Cell. Oct. 1982;30(3):933-43.
Mattanovich et al., Open access to sequence: browsing the Pichia pastoris genome. Microb Cell Fact. Oct. 16, 2009;8:53. doi: 10.1186/1475-2859-8-53.
Prabha et al., Identification of the dipeptidyl aminopeptidase responsible for N-terminal clipping of recombinant Exendin-4 precursor expressed in Pichia pastoris. Protein Expr Purif. Apr. 2009;64(2):155-61. doi: 10.1016/j.pep.2008.10.021. Epub Nov. 8, 2008.
Rakestraw et al., Directed evolution of a secretory leader for the improved expression of heterologous proteins and full-length antibodies in *Saccharomyces cerevisiae*. Biotechnol Bioeng. Aug. 15, 2009;103(6):1192-201. doi: 10.1002/bit.22338.
Sasagawa et al., High-throughput recombinant gene expression systems in Pichia pastoris using newly developed plasmid vectors. Plasmid. Jan. 2011;65(1):65-9. doi: 10.1016/j.plasmid.2010.08.004. Epub Aug. 31, 2010.
Werten et al., Reduced proteolysis of secreted gelatin and Yps1-mediated alpha-factor leader processing in a Pichia pastoris kex2 disruptant. Appl Environ Microbiol. May 2005;71(5):2310-7.

*Primary Examiner* — Jim Ketter
(74) *Attorney, Agent, or Firm* — Wolf, Greenfield & Sacks, P.C.

(57) ABSTRACT

Methods are provided for the expression of immunoglobulin variable domains that are secreted into the culture medium. The methods provide for the production of homogeneous immunoglobulin variable domains in which the proportion of product-related variants that comprise, at the N-terminus, at least one redundant amino acid residue derived from the secretion signal is strongly reduced or absent.

22 Claims, 3 Drawing Sheets

METHOD FOR THE PRODUCTION OF IMMUNOGLOBULIN SINGLE VARIABLE DOMAINS

RELATED APPLICATIONS

Figure 1:
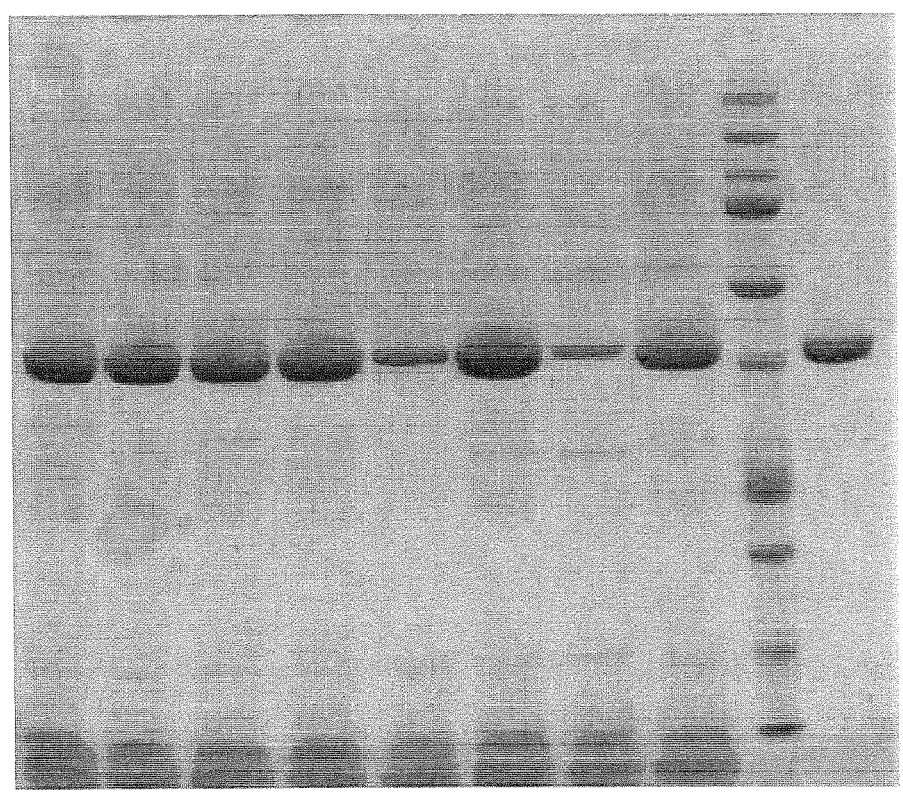

This application is a national stage filing under 35 U.S.C. §371 of international application PCT/EP2012/058525, filed May 9, 2012, which was published under PCT Article 21(2) in English, and claims the benefit under 35 U.S.C. §119(e) of U.S. provisional application Ser. No. 61/484,109, filed May 9, 2011, the disclosures of which are incorporated by reference herein in their entireties.

FIELD OF THE INVENTION

The present invention relates to the expression and/or production of immunoglobulin variable domains. More specifically, the present invention relates to methods for the manufacture of immunoglobulin variable domains, in yeast strains, in particular *Pichia pastoris* yeast strains. In particular, the present invention relates to a method for producing homogeneous immunoglobulin variable domains in which the proportion of product-related variants that comprise at least one redundant amino acid residue at the N-terminus is strongly reduced or absent.

The immunoglobulin variable domains produced according to the invention are superior in terms of product homogeneity because the amount of product-related variant is reduced or absent. This is beneficial e.g. in the context of a therapeutic application of the immunoglobulin variable domains.

The invention also relates to secretion signal sequences for use in the methods of the invention; to nucleic acids encoding such secretion signal sequences; and to host cells comprising such nucleic acids, and/or expressing and/or processing or capable of expressing and/or processing such secretion signal sequences.

Other aspects, embodiments, advantages and applications of the invention will become clear from the further description herein.

BACKGROUND ART

For therapeutic applications, immunoglobulins must be of very high product quality. This requires, amongst others, homogeneity in structural terms. Moreover, the production costs are strongly influenced by difficulties encountered during the production process. For example, difficulties to separate structural variants of the desired protein will necessitate complex and costly purification strategies. Lack of homogeneity will impact the economics of the production process and hence, the costs for the therapeutic overall. Lack of homogeneity may also increase undesired properties of the immunoglobulin, such as the immunogenicity.

Heterologous expression of biopharmaceuticals is common. The transformation and manipulation of well-studied hosts such as *Escherichia coli* or *Saccharomyces cerevisiae* draw on many genetic tools and strains and a plethora of research into regulatory responses and protein functions. Non-conventional yeasts, in particular *Pichia pastoris*, have found wide application in heterologous expression because they produce very high levels of heterologous proteins, secrete proteins, or exhibit more versatile substrate utilization. However, relatively few genetic tools, engineered strains and data on the biology of these organisms are available.

When over-expressing in a host a protein destined for secretion from the host into the culture medium, the secretion of the protein can be achieved by fusing the protein to a secretion signal sequence that directs the passage of the polypeptide through the endoplasmic reticulum and the Golgi apparatus and that is cleaved from the polypeptide by a signal peptidase before being packaged into secretory vesicles, which fuse with the plasma membrane to release the processed protein.

A secretion signal sequence that has been used to produce a variety of secreted proteins in yeast expression systems is the signal sequence of the prepro-polyprotein precursor of the *S. cerevisiae* mating pheromone alpha-factor (aMF secretion signal peptide; Kurjan and Herskowitz 1982, Cell 30: 933-943; Sasagawa et al. 2011, Plasmid 65(1): 65-69).

While the use of the aMF secretion signal peptide most often results in secretion of the proteins from the yeast strains, it has been observed that the proteins are not always correctly processed. For example, WO 2002/086101 describes that the expression in *Hansenula polymorpha* and *Saccharomyces cerevisiae* of HCV envelope proteins using the alpha-mating factor leader sequence of *S. cerevisiae* leads to several expression products with a different aminoterminus in addition to the main product. WO 2007/148345 describes that the expression in *Pichia pastoris* of recombinant Exendin-4 using the alpha factor signal sequence and propeptide results, in addition to the main product, in molecules that are clipped, lacking the first two amino acids from the N-terminus.

During secretion of the alpha mating factor signal sequence from *S. cerevisiae*, the signal peptide is removed by two processing enzymes. The enzyme Kex2 cleaves after a specific lysine-arginine, then Ste13 clips off the dipeptides EA and EA to yield the mature alpha mating factor (Fuller et al. 1988, Annu. Rev. Physiol. 50: 345-362). Esposito et al. 2005 (Prot. Expr. and Purif. 40: 424-428) observed that while the *Pichia* homolog of Kex2 could cleave at the expected site, the Ste13 homolog did not, resulting in N-terminal extension of amino acid residues EAEA derived from the secretion signal sequence. They stated that inefficient Ste13 processing of the alpha mating factor signal peptide in *Pichia* is common.

Ghosalkar et al. 2008 (Protein Expr. Purif. 60(2): 103-109) also describe that the expression in *Pichia pastoris* of human interferon-alpha 2b (IFN-alpha2b) using, amongst others, the full *Saccharomyces cerevisiae* MF-alpha factor prepro sequence resulted, in addition to the main product, in two molecules with a different N-terminus due to inefficient processing of the secretion signal. However, the alpha prepro sequence without the EAEA repeats (i.e. with only the Kex2 cleavage site) directed the secretion of maximum amount of IFN-alpha2b into the culture medium, with the same amino terminal sequence as the native protein.

In contrast to the difficulties described above, immunoglobulin single variable domains can be readily expressed in *P. pastoris*. Immunoglobulin single variable domains are characterized by formation of the antigen binding site by a single variable domain, which does not require interaction with a further domain (e.g. in the form of VH/VL interaction) for antigen recognition. Production of Nanobodies, as one specific example of an immunoglobulin single variable domain, has been extensively described e.g. in WO 94/25591 and is known to result in good quality product. Moreover, as outlined in WO 2010/125187, material produced in *P. pastoris* is characterized by equal functionality as compared to *E. coli* produced material. Up to now the problem of incompletely processed product being present in the final product has not yet been observed for immunoglobulin single variable domains.

SUMMARY OF THE INVENTION

The present invention is based on the unexpected observation that expression in *Pichia pastoris* of immunoglobulin single variable domains using the secretion signal sequence of the prepro-polyprotein precursor of the *S. cerevisiae* mating pheromone alpha-factor (hereinafter also referred to as "aMF secretion signal sequence") resulted in a lower amount of intact immunoglobulin single variable domains than expected (based on the total amount of immunoglobulin single variable domains produced). Even the expression in *Pichia pastoris* of immunoglobulin single variable domains using the aMF secretion signal sequence with only the Kex2 cleavage site (i.e. without the EAEA repeats; SEQ ID NO: 1) still resulted in inefficient processing of the polypeptide. The expression and/or production of the immunoglobulin single variable domains using this aMF secretion signal sequence resulted in a fraction of immunoglobulin single variable domains comprising N-terminal extensions of amino acid residues derived from the aMF secretion signal sequence.

The present invention provides methods for the expression and/or production of secreted immunoglobulin variable domains, or secreted immunoglobulin single variable domains, which overcome this unexpected problem. In one aspect, the present invention provides improved methods for the expression and/or production of secreted immunoglobulin variable domains, preferably secreted immunoglobulin single variable domains, characterized in that less than about 5% of the immunoglobulin variable domains comprise N-terminal extensions of amino acid residues derived from the secretion signal sequence. More particularly, the present invention provides methods for the expression and/or production of secreted polypeptides (also referred to as "polypeptides of the invention") comprising one or more immunoglobulin variable domains, preferably immunoglobulin single variable domains, the secretion of which is induced by fusing the polypeptides to a secretion signal sequence, said methods comprising the steps of:
  a) maintaining a host under conditions that are such that said host expresses and/or produces the polypeptides;
  b) isolating and/or purifying the secreted polypeptides from the medium;
wherein less than about 5% of the secreted polypeptides isolated and/or purified in step b) contains N-terminal extensions of amino acid residues derived from the secretion signal sequence, as determined by mass spectrometry.

Preferably, less than about 3.5%, more preferably less than about 2.5%, even more preferably less than about 2% of the polypeptides isolated and/or purified in step b) contains N-terminal extensions of amino acid residues derived from the secretion signal sequence, as determined by mass spectrometry.

The present inventors surprisingly observed that the expression and/or production of immunoglobulin single variable domains, the secretion of which is induced by fusing the polypeptide to the native aMF secretion signal sequence of SEQ ID NO: 1, resulted in a lower amount (about 92% or less) of intact immunoglobulin single variable domains than expected (based on the total amount of immunoglobulin single variable domains produced).

Accordingly, in another aspect, the present invention provides methods for the expression and/or production of secreted immunoglobulin variable domains, preferably secreted immunoglobulin single variable domains, with a secretion signal sequence that is different from the native aMF secretion signal sequence (as further defined herein). More particularly, the present invention provides methods for the expression and/or production of secreted polypeptides comprising one or more immunoglobulin variable domains, preferably immunoglobulin single variable domains, the secretion of which is induced by fusing the polypeptides to a secretion signal sequence, said methods comprising the steps of:
  a) maintaining a host under conditions that are such that said host expresses and/or produces the polypeptide;
  b) isolating and/or purifying the secreted polypeptide from the medium;
wherein less than about 5% of the secreted polypeptides isolated and/or purified in step b) contains N-terminal extensions of amino acid residues derived from the secretion signal sequence, as determined by mass spectrometry; and wherein the secretion signal sequence is different from the native aMF secretion signal sequence.

More particularly, the present invention provides methods for the expression and/or production of secreted polypeptides comprising one or more immunoglobulin variable domains, preferably immunoglobulin single variable domains, the secretion of which is induced by fusing the polypeptides to a secretion signal sequence that is different from the native aMF secretion signal sequence, said methods comprising the steps of:
  a) maintaining a host under conditions that are such that said host expresses and/or produces the polypeptide;
  b) isolating and/or purifying the secreted polypeptide from the medium;
wherein less than about 5% of the secreted polypeptides isolated and/or purified in step b) contains N-terminal extensions of amino acid residues derived from the secretion signal sequence, as determined by mass spectrometry.

The present inventors further observed that the expression and/or production of immunoglobulin single variable domains, the secretion of which is induced by fusing the polypeptide to the native aMF secretion signal sequence of SEQ ID NO: 1, resulted in different lengths of N-terminal extensions of amino acid residues derived from the native aMF secretion signal sequence of SEQ ID NO: 1. The different lengths of N-terminal extensions of amino acid residues derived from the native aMF secretion signal sequence of SEQ ID NO: 1 resulted from the cleavage of the secretion signal sequence at different non-canonical cleavage sites present in the native aMF secretion signal sequence of SEQ ID NO: 1.

Accordingly, in yet another aspect, the present invention provides methods for the expression and/or production of secreted immunoglobulin variable domains, preferably secreted immunoglobulin single variable domains, with a modified aMF secretion signal sequence. More specifically, the aMF secretion signal sequence is modified at one or more non-canonical cleavage sites that are present in the native aMF secretion signal sequence and that result in the production of N-terminal extensions of amino acid residues derived from the native aMF secretion signal sequence, as determined by mass spectrometry. More particularly, the present invention provides methods for the expression and/or production of secreted polypeptides comprising one or more immunoglobulin variable domains, preferably immunoglobulin single variable domains, the secretion of which is induced by fusing the polypeptide to a secretion signal sequence, said methods comprising the steps of:

a) maintaining a host under conditions that are such that said host expresses and/or produces the polypeptides;
b) isolating and/or purifying the secreted polypeptides from the medium;

wherein less than about 5% of the secreted polypeptides isolated and/or purified in step b) contain N-terminal extensions of amino acid residues derived from the secretion signal sequence, as determined by mass spectrometry; and wherein the secretion signal sequence is an aMF secretion signal sequence modified at one or more non-canonical cleavage sites that are present in the native aMF secretion signal sequence and that result in the production of N-terminal extensions of amino acid residues derived from the native aMF secretion signal sequence, as determined by mass spectrometry.

More particularly, the present invention provides methods for the expression and/or production of secreted polypeptides comprising one or more immunoglobulin variable domains, preferably immunoglobulin single variable domains, the secretion of which is induced by fusing the polypeptide to an aMF secretion signal sequence modified at one or more non-canonical cleavage sites that are present in the native aMF secretion signal sequence and that result in the production of N-terminal extensions of amino acid residues derived from the native aMF secretion signal sequence, as determined by mass spectrometry, said methods comprising the steps of:
a) maintaining a host under conditions that are such that said host expresses and/or produces the polypeptides;
b) isolating and/or purifying the secreted polypeptides from the medium;

wherein less than about 5% of the secreted polypeptides isolated and/or purified in step b) contain N-terminal extensions of amino acid residues derived from the secretion signal sequence, as determined by mass spectrometry.

In one embodiment, the aMF secretion signal sequence is modified by substituting one or more of the amino acid residues flanking the non-canonical cleavage sites present in the native aMF secretion signal sequence for another amino acid residue or by deleting one or more of the amino acid residues flanking the non-canonical cleavage sites present in the native aMF secretion signal sequence.

The present inventors in particular observed that the expression and/or production of immunoglobulin single variable domains, the secretion of which is induced by fusing the polypeptide to the native aMF secretion signal sequence of SEQ ID NO: 1 resulted in N-terminal extensions of 2, 3, 7, 9, 11, 12, 13, 14 and 21 amino acid residues derived from the native aMF secretion signal sequence of SEQ ID NO: 1, in particular derived from position 84-85, 83-85, 79-85, 77-85, 75-85, 74-85, 73-85, 72-85 and 65-85, respectively, of SEQ ID NO: 1.

Accordingly, in a further aspect, the present invention provides methods for the expression and/or production of secreted immunoglobulin variable domains, preferably secreted immunoglobulin single variable domains, with an aMF secretion signal sequence modified at one or more non-canonical cleavage sites corresponding to the non-canonical cleavage sites that are present in the native aMF secretion signal sequence of SEQ ID NO: 1 and that result in the production of N-terminal extensions of 2, 3, 7, 9, 11, 12, 13, 14 or 21 amino acid residues derived from the native aMF secretion signal sequence of SEQ ID NO: 1, in particular that result in the production of N-terminal extensions of 2, 3, 7, 9, 11, 12, 13, 14 or 21 amino acid residues derived from position 84-85, 83-85, 79-85, 77-85, 75-85, 74-85, 73-85, 72-85 and 65-85, respectively, of SEQ ID NO: 1.

More particularly, the present invention provides methods for the expression and/or production of secreted polypeptides comprising one or more immunoglobulin variable domains, preferably immunoglobulin single variable domains, the secretion of which is induced by fusing the polypeptide to a secretion signal sequence, said methods comprising the steps of:
a) maintaining a host under conditions that are such that said host expresses and/or produces the polypeptides;
b) isolating and/or purifying the secreted polypeptides from the medium;

wherein less than about 5% of the secreted polypeptides isolated and/or purified in step b) contain N-terminal extensions of amino acid residues derived from the secretion signal sequence, as determined by mass spectrometry; and wherein the secretion signal sequence is an aMF secretion signal sequence modified at one or more non-canonical cleavage sites corresponding to the non-canonical cleavage sites that are present in the native aMF secretion signal sequence of SEQ ID NO: 1 and that result in the production of N-terminal extensions of 2, 3, 7, 9, 11, 12, 13, 14 or 21 amino acid residues derived from the native aMF secretion signal sequence of SEQ ID NO: 1, in particular that result in the production of N-terminal extensions of 2, 3, 7, 9, 11, 12, 13, 14 or 21 amino acid residues derived from position 84-85, 83-85, 79-85, 77-85, 75-85, 74-85, 73-85, 72-85 and 65-85, respectively, of SEQ ID NO: 1.

More particularly, the present invention provides methods for the expression and/or production of secreted polypeptides comprising one or more immunoglobulin variable domains, preferably immunoglobulin single variable domains, the secretion of which is induced by fusing the polypeptide to an aMF secretion signal sequence modified at one or more non-canonical cleavage sites corresponding to the non-canonical cleavage sites that are present in the native aMF secretion signal sequence of SEQ ID NO: 1 and that result in the production of N-terminal extensions of 2, 3, 7, 9, 11, 12, 13, 14 or 21 amino acid residues derived from the native aMF secretion signal sequence of SEQ ID NO: 1, in particular that result in the production of N-terminal extensions of 2, 3, 7, 9, 11, 12, 13, 14 or 21 amino acid residues derived from position 84-85, 83-85, 79-85, 77-85, 75-85, 74-85, 73-85, 72-85 and 65-85, respectively, of SEQ ID NO: 1, said methods comprising the steps of:
a) maintaining a host under conditions that are such that said host expresses and/or produces the polypeptides;
b) isolating and/or purifying the secreted polypeptides from the medium;

wherein less than about 5% of the secreted polypeptides isolated and/or purified in step b) contain N-terminal extensions of amino acid residues derived from the secretion signal sequence, as determined by mass spectrometry.

In one embodiment, the aMF secretion signal sequence is modified by substituting one or more of the amino acid residues flanking the non-canonical cleavage sites corresponding to the non-canonical cleavage sites that are present in the native aMF secretion signal sequence in SEQ ID NO: 1 for another amino acid residue, or by deleting one or more of the amino acid residues flanking the non-canonical cleavage sites corresponding to the non-canonical cleavage sites that are present in the native aMF secretion signal sequence in SEQ ID NO: 1.

In one aspect of the embodiment, the aMF secretion signal sequence is modified at one or more amino acid positions corresponding to the following amino acid positions in SEQ ID NO: 1: amino acid position 64, 65, 66, 71, 72, 73, 74, 75, 76, 77, 78, 79, 80, 82, 83, 84 and 85 of SEQ ID NO: 1, in particular at one or more of amino acid positions 76, 77 and 78 of SEQ ID NO: 1.

In another aspect of the embodiment, one or more of the amino acid residues at the amino acid positions corresponding to amino acid positions 64, 65, 66, 71, 72, 73, 74, 75, 76, 77, 78, 79, 80, 82, 83, 84 and 85 of SEQ ID NO: 1, in particular amino acid positions 76, 77 and 78 of SEQ ID NO: 1, are substituted for another amino acid residue or deleted.

In still another aspect of the embodiment, the aMF secretion signal sequence is modified by one or more amino acid modifications corresponding to one or more of the following amino acid modifications in SEQ ID NO: 1: K76R, K76H, K76A, K76P, K76del, E77T, E77A and 76KEE/AGI.

In a further embodiment, the aMF secretion signal sequence that is modified comprises or consists of SEQ ID NO: 1.

In one aspect of the embodiment, the modified aMF secretion signal sequence, used in the method of the invention, comprises or consists of any one of the amino acid sequences of SEQ ID NO: 2 to 9.

The present inventors further found that the expression and/or production of immunoglobulin single variable domains, the secretion of which is induced by fusing the polypeptide to a secretion signal sequence from *Pichia pastoris*, did not result in detectable amounts of immunoglobulin single variable domains comprising N-terminal extensions of amino acid residues derived from the secretion signal sequence.

Accordingly, in another aspect, the present invention provides methods for the expression and/or production of secreted immunoglobulin variable domains, preferably secreted immunoglobulin single variable domains, with a secretion signal sequence from *Pichia pastoris*. More particularly, the present invention provides methods for the expression and/or production of secreted polypeptides comprising one or more immunoglobulin variable domains, preferably immunoglobulin single variable domains, the secretion of which is induced by fusing the polypeptides to a secretion signal sequence, said methods comprising the steps of:
  a) maintaining a host under conditions that are such that said host expresses and/or produces the polypeptides;
  b) isolating and/or purifying the secreted polypeptides from the medium;
wherein less than about 5% of the secreted polypeptide isolated and/or purified in step b) contains N-terminal extensions of amino acid residues derived from the secretion signal sequence, as determined by mass spectrometry; and wherein the secretion signal sequence is a secretion signal sequence from *Pichia pastoris*.

More particularly, the present invention provides methods for the expression and/or production of secreted polypeptides comprising one or more immunoglobulin variable domains, preferably immunoglobulin single variable domains, the secretion of which is induced by fusing the polypeptides to a secretion signal sequence from *Pichia pastoris*, said methods comprising the steps of:
  a) maintaining a host under conditions that are such that said host expresses and/or produces the polypeptides;
  b) isolating and/or purifying the secreted polypeptides from the medium;
wherein less than about 5% of the secreted polypeptide isolated and/or purified in step b) contains N-terminal extensions of amino acid residues derived from the secretion signal sequence, as determined by mass spectrometry.

In one embodiment, the *Pichia pastoris* secretion signal sequence comprises or consists of any one of the amino acid sequence of SEQ ID NO: 10 to 46, in particular of SEQ ID NO: 17 or 38.

The host used for the expression and or production of the polypeptides of the invention may be selected from prokaryotic hosts or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*.

The immunoglobulin (single) variable domain expressed and/or produced in the method of the present invention may be, without being limiting, an immunoglobulin (single) variable domain that is a light chain variable domain sequence or a heavy chain variable domain sequence, more specifically an immunoglobulin (single) variable domain which is a heavy chain variable domain sequence that is derived from a conventional four-chain antibody or a heavy chain variable domain sequence that is derived from a heavy chain antibody, in particular a domain antibody (or an amino acid sequence that is suitable for use as a domain antibody), a single domain antibody (or an amino acid sequence that is suitable for use as a single domain antibody), a "dAb" (or an amino acid sequence that is suitable for use as a dAb) or a Nanobody (including but not limited to a VHH sequence), preferably a Nanobody.

In a further aspect of the invention, the secreted polypeptide of the invention, comprising one or more immunoglobulin (single) variable domains, is coupled to one or more groups, residues or moieties. Accordingly, the present invention also relates to a method for the expression and/or production of a compound comprising a polypeptide of the invention coupled to one or more groups, residues or moieties, said method comprising the steps of:
  a) maintaining a host under conditions that are such that said host expresses and/or produces secreted polypeptides comprising one or more immunoglobulin variable domains;
  b) isolating and/or purifying the polypeptides from the medium, wherein less than about 5% of the polypeptides isolated and/or purified contains N-terminal extensions of amino acid residues derived from the secretion signal sequence, as determined by mass spectrometry;
  c) coupling one or more groups, residues or moieties to the polypeptides.

Preferably, less than about 3.5%, more preferably less than about 2.5%, even more preferably less than about 2% of the polypeptides isolated and/or purified in step b) contains N-terminal extensions of amino acid residues derived from the secretion signal sequence, as determined by mass spectrometry.

The invention also relates to the secretion signal sequences for use in the methods of the invention; to polypeptides of the invention fused to such secretion signal sequences; to nucleic acids encoding such secretion signal sequences; to nucleic acids encoding the polypeptides of the invention fused to such secretion signal sequences; and to host cells comprising such nucleic acids, expressing and/or processing or capable of expressing and/or processing such secretion signal sequences, and/or expressing and/or processing or capable of expressing and/or processing polypeptides of the invention fused to such secretion signal sequences.

FIGURE LEGENDS

FIG. 1: SDS-page analysis of partially purified, secreted Nanobody A produced by fusing the Nanobody A polypeptide to the native aMF secretion signal sequence of SEQ ID NO: 1 or to the modified aMF secretion signal sequences of SEQ ID NO: 2 to 9 (as indicated), and expression in small scale *P. pastoris* cultures (5 ml).

Figure 2:
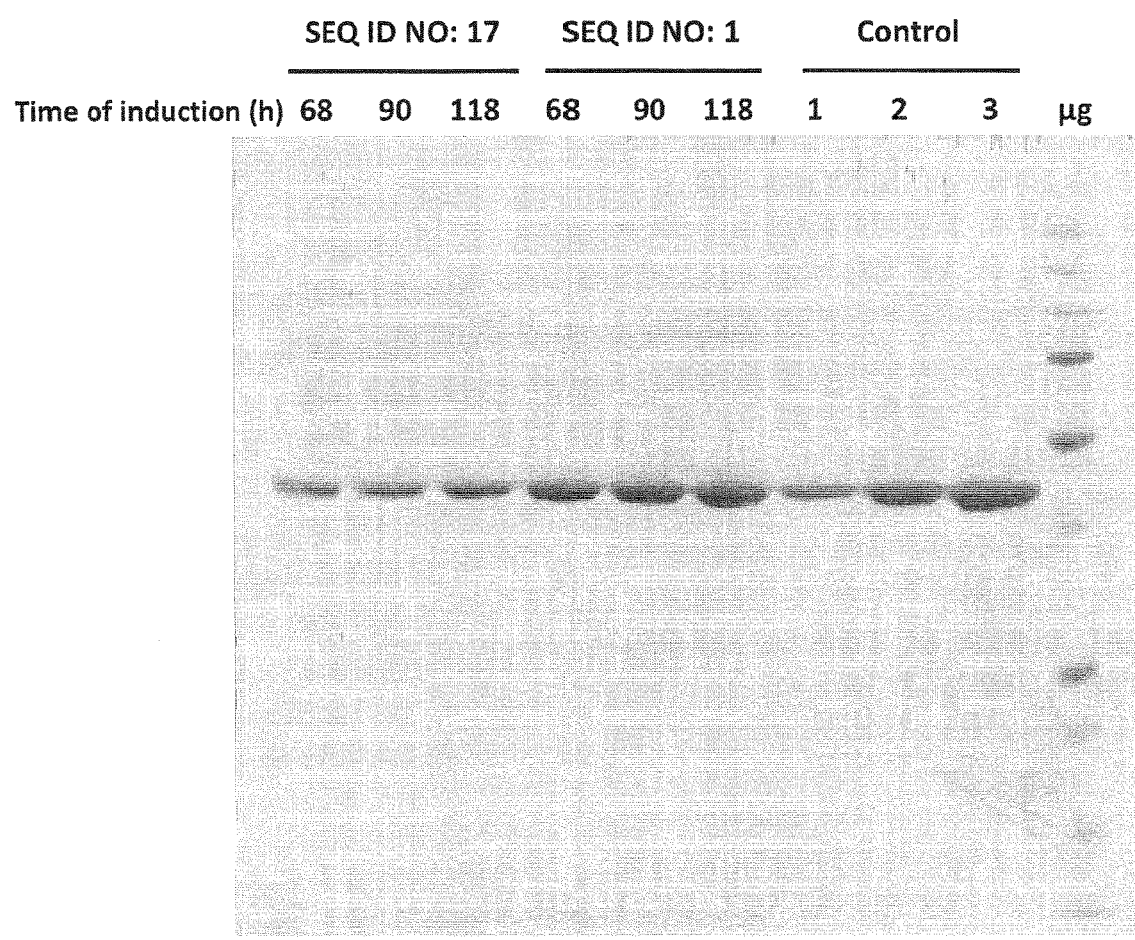

FIG. 2: SDS-page analysis of partially purified, secreted Nanobody A produced by fusing the Nanobody A polypeptide to the native aMF secretion signal sequence of SEQ ID NO: 1 or to the *Pichia pastoris* secretion signal sequences of SEQ ID NO: 17 and expression in glycerol-fed batches of *P. pastoris* as described in Example 5, Samples were taken after 68, 90 and 118 hours of induction (as indicated).

Figure 3:
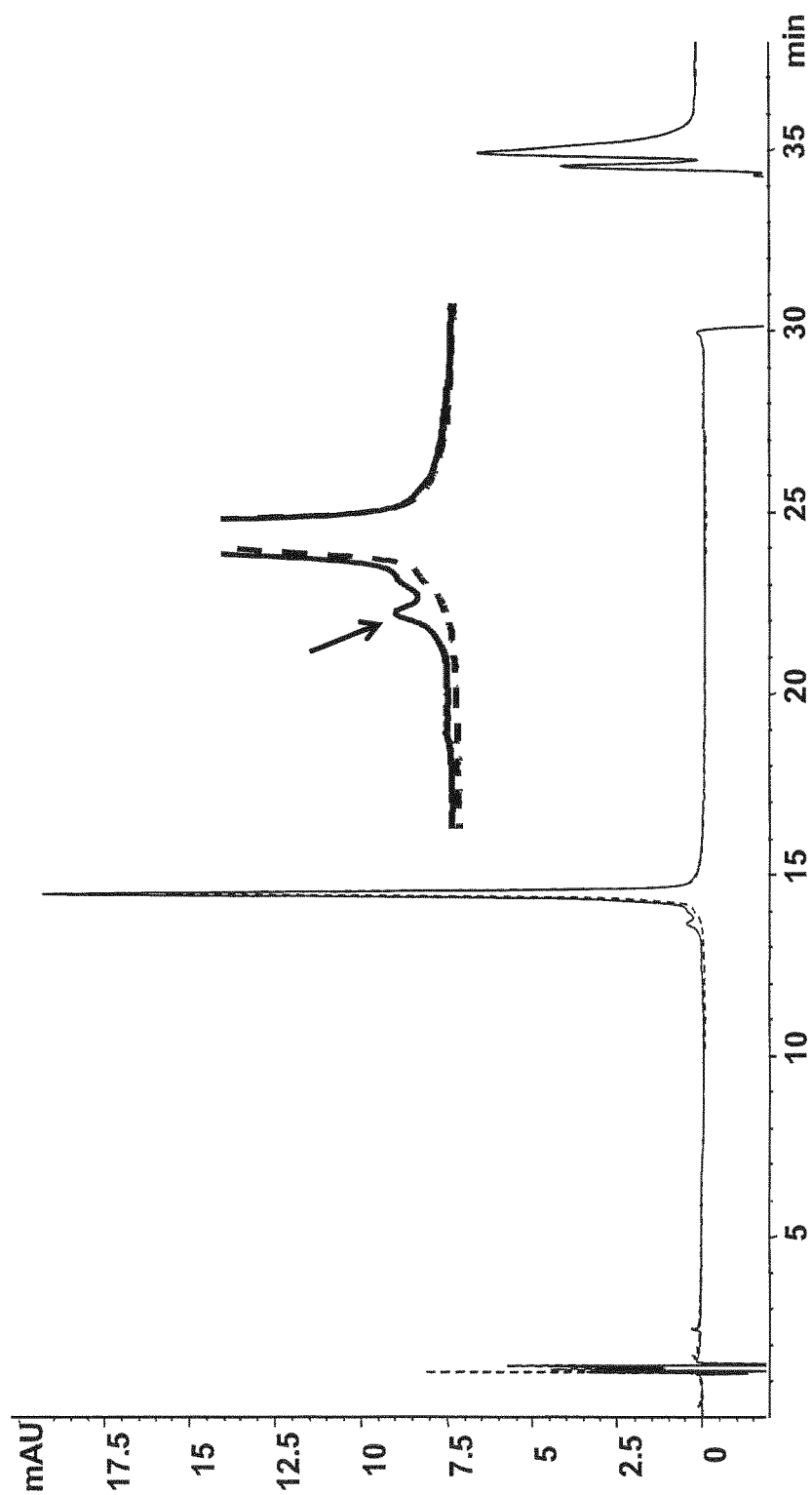

FIG. 3. Overlay of RP-HPLC chromatograms from LC-MS analysis of Nanobody A produced by fusing the Nanobody A polypeptide to the native aMF secretion signal sequence of SEQ ID NO: 1 (solid line) or to the *Pichia pastoris* secretion signal sequences of SEQ ID NO: 17 (dashed line). The overlay shows a distinct pre-peak (indicated with black arrow) corresponding to Nanobody A with incompletely processed secretion signal sequences for the first chromatogram (solid line) and no pre-peak for the second (dashed line).

DETAILED DESCRIPTION

Unless indicated or defined otherwise, all terms used have their usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, UK (2001); and Janeway et al., "Immunobiology" (6th Ed.), Garland Science Publishing/Churchill Livingstone, New York (2005), as well as to the general background art cited herein.

The term "immunoglobulin variable domain" (or "variable domain") refers to the part or domain of an immunoglobulin molecule or antibody which is partially or fully responsible for antigen binding. The term "immunoglobulin single variable domain" (or "single variable domain"), defines molecules wherein the antigen binding site is present on, and formed by, a single immunoglobulin domain. This sets immunoglobulin single variable domains apart from "conventional" immunoglobulins or their fragments, wherein two immunoglobulin domains, in particular two "immunoglobulin variable domains" interact to form an antigen binding site. Typically, in conventional immunoglobulins, a heavy chain variable domain (VH) and a light chain variable domain ($V_L$) interact to form an antigen binding site. In this case, the complementarity determining regions (CDRs) of both $V_H$ and $V_L$ will contribute to the antigen binding site, i.e. a total of 6 CDRs will be involved in antigen binding site formation.

In contrast, the binding site of an immunoglobulin single variable domain is formed by a single VH or VL domain. Hence, the antigen binding site of an immunoglobulin single variable domain is formed by no more than three CDRs. The term "immunoglobulin single variable domain" does comprise fragments of conventional immunoglobulins wherein the antigen binding site is formed by a single variable domain.

Generally, immunoglobulin single variable domains will be amino acid sequences that consist of 4 framework regions (FR1 to FR4 respectively) and 3 complementarity determining regions (CDR1 to CDR3 respectively); or any suitable fragment of such an amino acid sequence (which will then usually contain at least some of the amino acid residues that form at least one of the CDR's). Such immunoglobulin single variable domains and fragments are most preferably such that they comprise an immunoglobulin fold or are capable for forming, under suitable conditions, an immunoglobulin fold. As such, the immunoglobulin single variable domain may for example comprise a light chain variable domain sequence (e.g. a $V_L$-sequence) or a suitable fragment thereof; or a heavy chain variable domain sequence (e.g. a $V_H$-sequence or $V_{HH}$ sequence) or a suitable fragment thereof; as long as it is capable of forming a single antigen binding unit (i.e. a functional antigen binding unit that consists of the immunoglobulin single variable domain, such that the single antigen binding domain does not need to interact with another variable domain to form a functional antigen binding unit, as is for example the case for the immunoglobulin variable domains that are present in for example conventional antibodies and scFv fragments that need to interact with another immunoglobulin variable domain—e.g. through a $V_H/V_L$ interaction—to form a functional antigen binding domain).

In one aspect of the invention, the immunoglobulin single variable domains are light chain variable domain sequences (e.g. a $V_L$-sequence), or heavy chain variable domain sequences (e.g. a $V_H$-sequence); more specifically, the immunoglobulin single variable domains can be heavy chain variable domain sequences that are derived from a conventional four-chain antibody or heavy chain variable domain sequences that are derived from a heavy chain antibody.

The immunoglobulin single variable domain may be a domain antibody (or an amino acid sequence that is suitable for use as a domain antibody), a single domain antibody (or an amino acid sequence that is suitable for use as a single domain antibody), a "dAb" or dAb (or an amino acid sequence that is suitable for use as a dAb) or a Nanobody® (as defined herein, and including but not limited to a $V_{HH}$ sequence) [Note: Nanobody® and Nanobodies® are registered trademarks of Ablynx N.V.]; other immunoglobulin single variable domains, or any suitable fragment of any one thereof. For a general description of (single) domain antibodies, reference is also made to the prior art cited herein, as well as to EP 0 368 684. For the term "dAb's", reference is for example made to Ward et al. 1989 (Nature 341 (6242): 544-546), to Holt et al. 2003 (Trends Biotechnol. 21(11): 484-490); as well as to for example WO 04/068820, WO 06/030220, WO 06/003388 and other published patent applications of Domantis Ltd. It should also be noted that, although less preferred in the context of the present invention because they are not of mammalian origin, immunoglobulin single variable domains can be derived from certain species of shark (for example, the so-called "IgNAR domains", see for example WO 05/18629).

In particular, the polypeptide of the invention may comprise or consist of a Nanobody or a suitable fragment thereof. For a further description of $V_{HH}$'s and Nanobodies, reference is made to the review article by Muyldermans 2001 (Reviews in Molecular Biotechnology 74: 277-302); as well as to the following patent applications, which are mentioned as general background art: WO 94/04678, WO 95/04079 and WO 96/34103 of the Vrije Universiteit Brussel; WO 94/25591, WO 99/37681, WO 00/40968, WO 00/43507, WO 00/65057, WO 01/40310, WO 01/44301, EP 1 134 231 and WO 02/48193 of Unilever; WO 97/49805, WO 01/21817, WO 03/035694, WO 03/054016 and WO 03/055527 of the Vlaams Instituut voor Biotechnologie (VIB); WO 03/050531 of Algonomics N.V. and Ablynx N.V.; WO 01/90190 by the National Research Council of Canada; WO 03/025020 (=EP 1 433 793) by the Institute of Antibodies; as well as WO 04/041867, WO 04/041862, WO 04/041865, WO 04/041863, WO 04/062551, WO 05/044858, WO 06/40153, WO 06/079372, WO 06/122786, WO 06/122787 and WO 06/122825, by Ablynx N.V. and the further published patent applications by Ablynx N.V. Reference is also made to the further prior art mentioned in these applications, and in particular to the list of references mentioned on pages 41-43 of the International application WO 06/040153, which list and references are incorporated herein by reference. As described in these references, Nanobodies (in particular $V_{HH}$ sequences and partially humanized Nanobodies) can in particular be characterized by the presence of one or more "Hallmark residues" in one or more of the framework sequences. A further description of the Nanobodies, including humanization and/or camelization of Nanobodies, as well as other modifications, parts or fragments, derivatives or "Nanobody fusions", multivalent constructs (including some non-limiting examples of linker sequences) and different modifications to increase the half-life of the Nanobodies and their preparations can be found e.g. in WO 08/101,985 and WO 08/142,164.

The total number of amino acid residues in a Nanobody can be in the region of 110-120, is preferably 112-115, and is most preferably 113. It should however be noted that parts, fragments, analogs or derivatives (as further described herein) of a Nanobody are not particularly limited as to their length and/or size, as long as such parts, fragments, analogs or derivatives meet the further requirements outlined herein and are also preferably suitable for the purposes described herein.

Thus, in the meaning of the present invention, the term "immunoglobulin single variable domain" comprises polypeptides which are derived from a non-human source, preferably a camelid, preferably a camelid heavy chain antibody. They may be humanized, as previously described. Moreover, the term comprises polypeptides derived from non-camelid sources, e.g. mouse or human, which have been "camelized", as previously described.

The term "immunoglobulin single variable domain" also encompasses variable domains of different origin, comprising mouse, rat, rabbit, donkey, human and camelid variable domains; as well as fully human, humanized or chimeric variable domains. For example, the invention comprises camelid variable domains and humanized camelid variable domains, or camelized variable domains, e.g. camelized dAb as described by Ward et al (see for example WO 94/04678 and Davies and Riechmann 1994 (FEBS Lett. 339(3): 285-290) and 1996 (Protein Eng. 9(6): 531-537)). Moreover, the invention comprises fused variable domains, e.g. forming a multivalent and/or multispecific construct (for multivalent and multispecific polypeptides containing one or more $V_{HH}$ domains and their preparation, reference is also made to Conrath et al. 2001 (J. Biol. Chem. 276: 7346-7350) as well as to for example WO 96/34103 and WO 99/23221).

Unless indicated otherwise, the term "immunoglobulin sequence"—whether used herein to refer to a heavy chain antibody or to a conventional 4-chain antibody—is used as a general term to include both the full-size antibody, the individual chains thereof, as well as all parts, domains or fragments thereof (including but not limited to antigen-binding domains or fragments such as $V_{HH}$ domains or $V_H/V_L$ domains, respectively). The terms antigen-binding molecules or antigen-binding protein are used interchangeably with immunoglobulin sequence, and include Nanobodies.

The immunoglobulin single variable domains provided by the invention are preferably in isolated form (as defined herein), or form part of a polypeptide of the invention (as defined herein), which may comprise or consist of one or more immunoglobulin single variable domains and which may optionally further comprise one or more further amino acid sequences (all optionally linked via one or more suitable linkers). For example, and without limitation, the one or more immunoglobulin single variable domains may be used as a binding unit in such a polypeptide, which may optionally contain one or more further amino acid sequences that can serve as a binding unit (i.e. against one or more other targets), so as to provide a monovalent, multivalent or multispecific polypeptide of the invention, respectively as e.g. described in WO 08/101,985, WO 08/142,164, WO 09/068,625, WO 09/068,627 and WO 08/020,079. Such a protein or polypeptide may also be in isolated form (as defined herein) and the methods of the present invention for the expression and/or production of immunoglobulin single variable domains equally apply to polypeptides comprising one or more immunoglobulin single variable domains.

According to the invention, the term "immunoglobulin single variable domain" may comprise constructs comprising two or more antigen binding units in the form of immunoglobulin single variable domain, as outlined above. For example, two (or more) immunoglobulin (single) variable domains with the same or different antigen specificity can be linked to form e.g. a bivalent, trivalent or multivalent construct. By combining immunoglobulin (single) variable domains of two or more specificities, bispecific, trispecific etc. constructs can be formed. For example, an immunoglobulin (single) variable domain according to the invention may comprise two immunoglobulin (single) variable domains directed against target A, and one immunoglobulin (single) variable domain against target B. Such constructs and modifications thereof, which the skilled person can readily envisage, are all encompassed by the term immunoglobulin (single) variable domain as used herein.

The invention in particular relates to secreted polypeptides comprising one or more immunoglobulin (single) variable domains. The term "secreted polypeptide", as used herein, refers to a polypeptide that is secreted from a host (as defined herein) into the culture medium. The secretion of the polypeptide is effected by fusing the polypeptide to a secretion signal sequence.

The term "secretion signal sequence" or "secretion signal peptide", as used herein, refers to an N-terminal peptide extension of a polypeptide that directs the secretion of the polypeptide, in particular, that directs the passage of the polypeptide through the endoplasmic reticulum and the Golgi apparatus and that is cleaved from the polypeptide by a signal peptidase (i.e., processing of the polypeptide) before being packaged into secretory vesicles, which fuse with the plasma membrane to release the processed protein (i.e., secretion of the polypeptide). In one embodiment of the present invention the polypeptides comprising one or more immunoglobulin (single) variable domains are attached to an N-terminal extension of amino acid residues derived from the secretion signal sequence. Such molecules are also referred to as "polypeptide of the invention" or "polypeptides of the invention".

"Polypeptide of the invention" or "polypeptides of the invention" thus refers to a secreted polypeptide comprising one or more immunoglobulin (single) variable domains, optionally attached to an N-terminal extension of amino acid residues derived from a secretion signal sequence. Accordingly, a "polypeptide of the invention" may be a polypeptide comprising one immunoglobulin (single) variable domain, optionally attached to an N-terminal extension of amino acid residues derived from a secretion signal sequence; and a "polypeptide of the invention" may be a polypeptide comprising two or more immunoglobulin (single) variable domains, optionally attached to an N-terminal extension of amino acid residues derived from a secretion signal sequence.

The terms "N-terminal extensions of amino acid residues derived from the secretion signal sequence" and "N-terminal extensions of amino acid residues from the secretion signal sequence" (both are used interchangeably) refer to amino acid residues derived from the C-terminal end of the secretion signal sequence fused to the polypeptide that are not cleaved off by signal peptidases and remain present at the N-terminal end of the polypeptide of the invention.

The present inventors surprisingly observed that the expression and/or production of a secreted polypeptide comprising one or more immunoglobulin variable domains, the secretion of which is induced by fusing the polypeptide to the aMF secretion signal sequence of SEQ ID NO: 1, resulted in a yield of about 5% or more of secreted polypeptide comprising N-terminal extensions of amino acid residues derived from the secretion signal sequence.

Accordingly, in one aspect, the present invention provides methods for the expression and/or production of secreted polypeptides comprising one or more immunoglobulin (single) variable domains, the secretion of which is induced by fusing the polypeptide to a secretion signal sequence, said methods comprising the steps of:
a) maintaining a host under conditions that are such that said host expresses and/or produces the polypeptides;
b) isolating and/or purifying the secreted polypeptides from the medium;
wherein less than about 5% of the secreted polypeptides isolated and/or purified in step b) contains N-terminal extensions of amino acid residues derived from the secretion signal sequence.

In one embodiment, the present invention relates to a method for the expression and/or production of secreted polypeptides comprising one or more immunoglobulin (single) variable domains, wherein the secretion of the polypeptides is induced by fusing the polypeptides to a secretion signal sequence that is different from the native aMF secretion signal sequence.

The term "(native) aMF secretion signal sequence", as used herein, refers to the secretion signal sequence of the prepro-polyprotein precursor of the Saccharomyces cerevisiae mating pheromone alpha-factor as described in Kurjan and Herskowitz (1982, Cell 30 (3): 933-943), and sequences derived therefrom that are capable of inducing the secretion of a polypeptide fused thereto in a yeast expression system. The alpha-factor is a tridecapeptide mating factor secreted by Saccharomyces alpha cells. The alpha-factor gene codes for four mature alpha-factor proteins within a precursor protein. The N-terminal end of the precursor protein contains a secretion signal sequence; the C-terminal half of the precursor protein contains four tandem copies of mature alpha-factor, each preceded by spacer peptides of six or eight amino acids (variations of Lys-Arg-Glu-Ala-Asp-Ala-Glu-Ala). More specifically, the term "(native) aMF secretion signal sequence", as used herein, refers to a secretion signal sequence comprising the N-terminal amino acids of the alpha-factor precursor protein capable of inducing the secretion of a polypeptide fused thereto in a yeast expression system. In a preferred aspect, the term "(native) aMF secretion signal sequence" refers to a secretion signal sequence comprising N-terminal amino acids of the alpha-factor precursor protein without the Glu-Ala-Glu-Ala repeats. (i.e. containing only the Kex2 cleavage site and not the Ste13 cleavage site). In particular, the term "(native) aMF secretion signal sequence", as used herein, refers to a secretion signal sequence comprising or consisting of SEQ ID NO: 1, and sequences derived therefrom that are capable of inducing the secretion of a polypeptide fused thereto in a yeast expression system. Accordingly, the secretion signal sequence may optionally comprise a spacer peptide of the precursor protein, such as the spacer peptide of the first mature alpha-factor contained in the precursor polypeptide, in particular a spacer peptide comprising 6 or 8 amino acids of the amino acid sequence Lys-Arg-Glu-Ala-(Asp-Ala)-Glu-Ala. In a preferred aspect, the secretion signal sequence does not contain the spacer peptide.

In another embodiment, the secretion of the polypeptides is induced by fusing the polypeptides to a modified aMF secretion signal sequence, in particular an aMF secretion signal sequence modified at one or more non-canonical cleavage sites that are present in the native aMF secretion signal sequence and that result in the production of N-terminal extensions of amino acid residues derived from the native aMF secretion signal sequence, as determined by mass spectrometry.

The term "non-canonical cleavage site", as used herein, refers to a site in a secretion signal peptide that is recognized and cleaved by a specific signal peptidase at a frequency that is rare compared to the frequency with which the canonical cleavage site is recognized and cleaved by that specific signal peptidase. The frequency with which a specific signal peptidase recognizes and cleaves a specific site in a secretion signal peptide can be determined, for example, by analyzing the statistical distribution of cleavage sites in a set of experimentally determined substrates of the specific signal peptidase. The "canonical cleavage site", as used herein, refers to a site in a secretion signal peptide that is statistically most frequently recognized and cleaved by a specific signal peptidase in a set of experimentally determined substrates of the specific signal peptidase.

The canonical cleavage site of the native aMF secretion signal sequence of SEQ ID NO: 1 is located C-terminal from the basic amino acid pair Lys-Arg at position 84-85 in SEQ ID NO: 1. This means that the native aMF secretion signal sequence of SEQ ID NO: 1 is expected to be cleaved most frequently from the alpha-factor precursor protein (or another polypeptide fused to the native aMF secretion signal sequence of SEQ ID NO: 1) C-terminal from the basic amino acid pair Lys-Arg. A non-canonical cleavage site of the native aMF secretion signal sequence of SEQ ID NO: 1 is a cleavage site different from the cleavage site located C-terminal from the basic amino acid pair Lys-Arg at position 84-85 in SEQ ID NO: 1. The native aMF secretion signal sequence of SEQ ID NO: 1 is expected to be cleaved only rarely from the alpha-factor precursor protein (or another polypeptide fused to the native aMF secretion signal sequence of SEQ ID NO: 1) at a non-canonical cleavage site, i.e. a cleavage site different from the cleavage site C-terminal from the basic amino acid pair Lys-Arg at position 84-85 in SEQ ID NO: 1.

Examples of non-canonical cleavage sites that are present in the native secretion signal sequence of SEQ ID NO: 1 are non-canonical cleavage sites that result in the production of N-terminal extensions of 2, 3, 7, 9, 11, 12, 13, 14 or 21 amino acid residues derived from the native secretion signal sequence of SEQ ID NO: 1.

In yet another embodiment of the invention, the secretion of the polypeptides is induced by fusing the polypeptides to an aMF secretion signal sequence modified at one or more non-canonical cleavage sites corresponding to the non-canonical cleavage sites that are present in the native aMF secretion signal sequence of SEQ ID NO: 1 and that result in the production of N-terminal extensions of 2, 3, 7, 9, 11, 12, 13, 14 or 21 amino acid residues derived from the native secretion signal sequence of SEQ ID NO: 1, as determined by mass spectrometry.

In one aspect, the aMF secretion signal sequence is modified by substituting one or more of the amino acid residues flanking the non-canonical cleavage sites corresponding to the non-canonical cleavage sites that are present in the native aMF secretion signal sequence in SEQ ID NO: 1 for another amino acid residue or by deleting one or more of the amino acid residues flanking the non-canonical cleavage sites corresponding to the non-canonical cleavage sites that are present in the native aMF secretion signal sequence in SEQ ID NO: 1.

In a further embodiment, the secretion of the polypeptide is induced by fusing the polypeptide to an aMF secretion signal sequence modified at one or more amino acid positions corresponding to one or more of amino acid positions 64, 65, 66, 71, 72, 73, 74, 75, 76, 77, 78, 79, 80, 82, 83, 84 and 85 of SEQ ID NO: 1, preferably one or more of amino acid positions 76, 77 and 78 of SEQ ID NO: 1.

Examples of amino acid modifications are substitutions and deletions of amino acid residues at one or more positions corresponding to one or more of position 64, 65, 66, 71, 72, 73, 74, 75, 76, 77, 78, 79, 80, 82, 83, 84 and 85 of SEQ ID NO: 1, in particular one or more amino acid modifications corresponding to one or more of amino acid modifications K76R, K76H, K76A, K76P, K76del, E77T, E77A and 76KEE/AGI in SEQ ID NO: 1.

In a specific embodiment, the aMF secretion signal sequence that is modified comprises or consists of SEQ ID NO: 1.

More specifically, the modified aMF secretion signal sequence may comprise or consist of any one of the amino acid sequences of SEQ ID NO: 2 to 9.

In yet another embodiment, the secretion of the polypeptides is induced by fusing the polypeptides to a secretion signal sequence from *Pichia pastoris*. The term "secretion signal sequence from *Pichia pastoris*" means that the respective secretion signal is naturally produced by *Pichia pastoris* (fused to one or more of its native proteins) and used for the secretion by *Pichia pastoris* of its native proteins. Without being limiting, the *Pichia pastoris* secretion signal sequence may comprise or consist of any one of the amino acid sequences of SEQ ID NO: 10 to 46, preferably SEQ ID NO: 17 or 38.

The presence of the N-terminal extensions of amino acid residues derived from the secretion signal sequence on the polypeptide of the invention and the percentage of polypeptides that contain N-terminal extensions of amino acid residues derived from the secretion signal sequence can be determined by any method know in the art for the determination of the presence of amino acid residues and/or of the amount, concentration, proportion or level of polypeptides, including but not limited to Liquid Chromatography such as Reverse Phase Chromatography or Ion Exchange Chromatography, and/or Mass spectrometry.

The method of the invention results in a reduced level (less than about 5%, preferably less than about 3.5%, more preferably less than about 2.5%, most preferably less than about 2%), or the complete absence, in the total amount of secreted polypeptides, of secreted polypeptides containing N-terminal extensions of amino acid residues derived from the secretion signal sequence. The method of the invention may result, for example, in 0-5%, more preferably 0-3.5%, 0-2.5%, 0-2% or 0-1% of secreted polypeptide containing N-terminal extensions of amino acid residues derived from the secretion signal sequence in the total amount of secreted polypeptides. Most preferably, the method of the present invention may result in secreted polypeptides that are free of polypeptides containing N-terminal extensions of amino acid residues derived from the secretion signal sequence. The proportion of secreted polypeptide containing N-terminal extensions of amino acid residues derived from the secretion signal sequence—as a % of the total—can be determined e.g. by Liquid Chromatography (LC) such as RP-HPLC or IE Chromatography or Mass Spectrometry (MS) as described herein.

The term "about x %" means that the proportion of polypeptides that contain N-terminal extensions of amino acid residues derived from the secretion signal sequence is x % of the total amount of polypeptides, wherein each value is understood to optionally encompass a range of ±0.5%.

The terms "host" and "host cells" are used interchangeably. In the method of the present invention any host can be used without limitation, provided that they are suitable for the production of immunoglobulin (single) variable domains. In particular, the present invention relates to the use of hosts wherein expression of secreted polypeptides comprising one or more immunoglobulin (single) variable domains, the secretion of which is induced by fusing the polypeptide to the aMF secretion signal sequence of SEQ ID NO: 1, results in a fraction of secreted polypeptides comprising N-terminal extensions of amino acid residues derived from the secretion signal sequence.

Specific examples of suitable hosts comprise prokaryotic organisms, such as coryneform bacteria or enterobacteriaceae. Also comprised are insect cells, in particular insect cells suitable for baculovirus mediated recombinant expression like *Trichoplusia* or *Spodoptera frugiperda* derived cells, including, but not limited to BTI-TN-5B1-4 High Five™ insect cells (Invitrogen), SF9 or Sf21 cells; mammalian cells like CHO cells and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*. Yeast is a preferable host of the present invention, and particularly preferred is *P. pastoris*.

In one aspect, the present invention relates to the use of non-*E. coli* hosts. In particular, the present invention relates to the use of non-*E. coli* hosts wherein expression of secreted polypeptides comprising one or more immunoglobulin (single) variable domains, the secretion of which is induced by fusing the polypeptides to the aMF secretion signal sequence of SEQ ID NO: 1, results in a fraction of secreted polypeptides comprising N-terminal extensions of amino acid residues derived from the secretion signal sequence. Accordingly, the host used for the expression and or production of the polypeptide of the invention may be selected from prokaryotic hosts other than *E. coli* or eukaryotic hosts, for example eukaryotic host selected from insect cells, mammalian cells, and lower eukaryotic hosts comprising yeasts such as *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus, Endomycopsis*, preferably *Pichia pastoris*.

The host used in the method of the present invention will be capable of producing the polypeptide of the invention. It will typically be genetically modified to comprise one or more nucleic acid sequences encoding the polypeptide of the invention. Non-limiting examples of genetic modifications comprise the transformation e.g. with a plasmid or vector, or the transduction with a viral vector. Some hosts can be genetically modified by fusion techniques. Genetic modifications include the introduction of separate nucleic acid molecules into a host, e.g. plasmids or vectors, as well as direct modifications of the genetic material of the host, e.g. by integration into a chromosome of the host, e.g. by homologous recombination. Oftentimes a combination of both will occur, e.g. a host is transformed with a plasmid, which, upon homologous recombination will (at least partly) integrate into the host chromosome. The skilled person knows suitable methods of genetic modification of the host to enable the host to produce immunoglobulin (single) variable domains.

General methods for producing immunoglobulin (single) variable domains and/or polypeptides comprising one or more immunoglobulin (single) variable domains in different hosts are known to the skilled person and/or have been described in the art. For example, production of Nanobodies in lower eukaryotic hosts such as *Pichia pastoris* has been extensively described in WO 94/25591. The contents of this application are explicitly referred to in the connection with general culturing techniques and methods, including suitable media and conditions. The contents of this document are incorporated by reference. The skilled person can also devise suitable genetic constructs for expression of the polypeptides of the invention in different hosts on the basis of the present application and common general knowledge. The present invention also relates to conditions and genetic constructs described in the art, for example the general culturing methods, plasmids, promoters and leader sequences described in WO 94/25591, WO 08/020,079, Gasser et al. 2006 (Biotechnol. Bioeng. 94: 535); Gasser et al. 2007 (Appl. Environ. Microbiol. 73: 6499); or Damasceno et al. 2007 (Microbiol. Biotechnol. 74: 381).

More particularly, the present invention provides a method for the expression and/or production of secreted polypeptides comprising one or more immunoglobulin (single) variable domains, the secretion of which is effected by fusing the polypeptides to a secretion signal sequence, said method at least comprising the steps of:
  a) cultivating a host or host cell (as defined herein) under conditions that are such that said host or host cell will multiply;
  b) maintaining said host or host cell under conditions that are such that said host or host cell expresses and/or produces the polypeptides;
  c) isolating and/or purifying the secreted polypeptides from the medium,
wherein less than about 5% of the secreted polypeptides isolated and/or purified in step c) contains N-terminal extensions of amino acid residues derived from the secretion signal sequence, as determined by mass spectrometry.

To produce/obtain expression of the polypeptides, the transformed host cell or transformed host organism may generally be kept, maintained and/or cultured under conditions such that the (desired) polypeptide is expressed/produced, Suitable conditions will be clear to the skilled person and will usually depend upon the host cell/host organism used, as well as on the regulatory elements that control the expression of the (relevant) nucleotide sequence. Again, reference is made to the handbooks and patent applications mentioned above.

Generally, suitable conditions may include the use of a suitable medium, the presence of a suitable source of food and/or suitable nutrients, the use of a suitable temperature, and optionally the presence of a suitable inducing factor or compound (e.g. when the nucleotide sequences of the invention are under the control of an inducible promoter); all of which may be selected by the skilled person. Again, under such conditions, the amino acid sequences of the invention may be expressed in a constitutive manner, in a transient manner, or only when suitably induced.

In a specific aspect, the host organism is kept, maintained and/or cultured under conditions that reduce the activity of the signal peptidase enzyme. Without being limiting, such conditions may include adjusting the pH during culturing and/or adjusting the culturing time.

The polypeptides of the invention may then be isolated from the host cell/host organism and/or from the medium in which said host cell or host organism was cultivated, using protein isolation and/or purification techniques known per se, such as (preparative) chromatography and/or electrophoresis techniques, differential precipitation techniques, affinity techniques (e.g. using a specific, cleavable amino acid sequence fused with the polypeptide of the invention) and/or preparative immunological techniques (i.e. using antibodies against the polypeptide to be isolated).

In the present invention, the host can be removed from the culture medium by routine means. For example, the host can be removed by centrifugation or filtration. The solution obtained by removal of the host from the culture medium is also referred to as culture supernatant, or clarified culture supernatant. The polypeptides of the invention can be purified from the culture supernatant by standard methods. Standard methods include, but are not limited to chromatographic methods, including size exclusion chromatography, hydrophobic chromatography, ion exchange chromatography, and affinity chromatography. These methods can be performed alone or in combination with other purification methods, e.g. precipitation or gel electrophoresis. The skilled person can devise suitable combinations of purification methods for the polypeptides of the invention on the basis of common general knowledge. For specific examples the art cited herein is referred to.

In one exemplary embodiment, the polypeptides of the invention can be purified from culture supernatant by a combination of affinity chromatography on Protein A, ion exchange chromatography and size exclusion chromatography. Reference to any "step of purification", includes, but is not limited to these particular methods.

More specifically, the polypeptides of the invention can be purified from culture supernatant using a process wherein the clarified supernatant (e.g. obtained by centrifugation) is captured on an affinity chromatography resin such as Protein A resin; followed by a polish step, which can comprise an CIEX or an AIEX step using for example Poros 50HS (POROS), SOURCE 30S or SOURCE 15S (GE Healthcare), SP Sepharose (GE Healthcare), Capto S (GE Healthcare) or Poros 50HQ (POROS), SOURCE 30Q or SOURCE 15Q (GE Healthcare), Q Sepharose (GE Healthcare), Capto Q and DEAE Sepharose (GE Healthcare), followed by a second polish step such as a Size exclusion chromatography step using for example Superdex 75 or Superdex 200 (GE Healthcare) followed by a final formulation step using TFF (UF/DF).

In a further aspect, the invention also relates to a method as described above comprising the further step of coupling or attaching one or more groups, residues or moieties to the polypeptide of the invention. Accordingly, the present invention relates to a method comprising the steps of:
- a) maintaining a host under conditions that are such that said host expresses and/or produces a secreted polypeptide comprising one or more immunoglobulin variable domains, the secretion of which is effected by fusing the polypeptide to a secretion signal sequence;
- b) isolating and/or purifying the secreted polypeptide from the medium wherein less than about 5% (preferably less than about 3.5%, more preferably less than about 2.5%, most preferably less than about 2%) of the secreted polypeptide isolated and/or purified contains N-terminal extensions of amino acid residues derived from the secretion signal sequence, as determined by mass spectrometry;
- c) coupling one or more groups, residues or moieties to the secreted polypeptide.

Examples of such groups, residues or moieties and methods and techniques that can be used to attach such groups, residues or moieties and the potential uses and advantages of such groups, residues or moieties will be clear to the skilled person.

In another aspect, the present invention relates to a method as described above, further comprising the step of processing the obtained polypeptide into a pharmaceutical unit dosage form and/or kit. Accordingly, the present invention relates to a method comprising the steps of:
- a) maintaining a host under conditions that are such that said host expresses and/or produces a secreted polypeptide comprising one or more immunoglobulin variable domains, the secretion of which is effected by fusing the polypeptide to a secretion signal sequence;
- b) isolating and/or purifying the secreted polypeptide from the medium wherein less than about 5% (preferably less than about 3.5%, more preferably less than about 2.5%, most preferably less than about 2%) of the secreted polypeptide isolated and/or purified contains N-terminal extensions of amino acid residues derived from the secretion signal sequence, as determined by mass spectrometry;
- c) processing the obtained polypeptide into a pharmaceutical unit dosage form and/or kit.

Without being limiting this further step c) may include the step of concentrating the polypeptide, exchanging it with a buffer and/or excipient and/or bringing the polypeptide into a sealed vial or container. The polypeptide of the invention can be prepared as unit dosage forms by preparing a (single dose) vial or container containing an aliquot of a (sterile) formulation comprising the polypeptide of the invention for a one time use. For example, a unit dosage of liquid formulation per vial may contain 1 mL, 2 mL, 3 mL, 4 mL, 5 mL, 6 mL, 7 mL, 8 mL, 9 mL, 10 mL, 15 mL, or 20 mL of a formulation comprising the polypeptide of the invention.

The pharmaceutical unit dosage forms can be made suitable for any form of delivery of the polypeptide of the invention including (without being limiting) parenteral delivery, topical delivery, pulmonary delivery, intranasal delivery, vaginal delivery, enteral delivery, rectal delivery, oral delivery and/or sublingual delivery. In one aspect, the pharmaceutical unit dosage form is made suitable for parenteral (such as e.g. intravenous, intraarterial, intramuscular, intracerebral, intraosseous, intradermal, intrathecal, intraperitoneal, subcutaneous, etc.) administration.

The method of the invention may also include the step of processing the polypeptide of the invention into a finished packaged and labelled pharmaceutical product or kit. This article of manufacture or kit includes the appropriate unit dosage form in an appropriate vessel or container such as a glass vial or other container that is hermetically sealed. In one embodiment, the unit dosage form is suitable for intravenous, intramuscular, intranasal, oral, topical or subcutaneous delivery. This step may also include the provision of instructions for use or other informational material that advise the physician, technician or patient on how to appropriately use the polypeptide of the invention.

The present invention further relates to the secretion signal sequences for use in the methods of the invention described above and to a polypeptide of the invention fused to such a secretion signal sequence.

The secretion signal sequence of the invention should be different from the native aMF secretion signal sequence. In a preferred aspect, the secretion signal sequence of the invention is different from SEQ ID NO: 1.

In another embodiment, the secretion signal sequence of the invention is a modified aMF secretion signal sequence, in particular an aMF secretion signal sequence modified at one or more non-canonical cleavage sites that are present in the native aMF secretion signal sequence and that, when fused to a polypeptide of the invention and expressed and processed by a host, result in the production of N-terminal extensions of amino acid residues derived from the native aMF secretion signal sequence, as determined by mass spectrometry. In a preferred aspect, the secretion signal sequence of the invention is a modified SEQ ID NO: 1, in particular SEQ ID NO: 1 modified at one or more non-canonical cleavage sites that are present in SEQ ID NO: 1 and that, when fused to a polypeptide of the invention and expressed and processed by a host, result in the production of N-terminal extensions of amino acid residues derived from SEQ ID NO: 1, as determined by mass spectrometry.

In yet another embodiment of the invention, the secretion signal sequence of the invention is an aMF secretion signal sequence modified at one or more non-canonical cleavage sites corresponding to the non-canonical cleavage sites that are present in the native aMF secretion signal sequence of SEQ ID NO: 1 and that, when fused to a polypeptide of the invention and expressed and processed by a host, result in the production of N-terminal extensions of 2, 3, 7, 9, 11, 12, 13, 14 or 21 amino acid residues derived from the native secretion signal sequence of SEQ ID NO: 1, as determined by mass spectrometry. In a preferred aspect, the secretion signal sequence of the invention is SEQ ID NO: 1 modified at one or more non-canonical cleavage sites that, when fused to a polypeptide of the invention and expressed and processed by a host, result in the production of N-terminal extensions of 2, 3, 7, 9, 11, 12, 13, 14 or 21 amino acid residues derived from the native secretion signal sequence of SEQ ID NO: 1, as determined by mass spectrometry.

In yet another embodiment of the invention, the secretion signal sequence of the invention is an aMF secretion signal sequence modified by substituting one or more of the amino acid residues flanking the non-canonical cleavage sites corresponding to the non-canonical cleavage sites that are present in the native aMF secretion signal sequence in SEQ ID NO: 1 for another amino acid residue, or by deleting one or more of the amino acid residues flanking the non-canonical cleavage sites corresponding to the non-canonical cleavage sites that are present in the native aMF secretion signal sequence in SEQ ID NO: 1. In a preferred aspect, the secretion signal sequence of the invention is SEQ ID NO: 1, modified by substituting one or more of the amino acid residues flanking the non-canonical cleavage sites present in SEQ ID NO: 1 for another amino acid residue, or by deleting one or more of the amino acid residues flanking the non-canonical cleavage sites present in the native aMF secretion signal sequence in SEQ ID NO: 1.

In a further embodiment, the secretion signal sequence of the invention is an aMF secretion signal sequence modified at one or more amino acid positions corresponding to one or more of amino acid positions 64, 65, 66, 71, 72, 73, 74, 75, 76, 77, 78, 79, 80, 82, 83, 84 and 85 of SEQ ID NO: 1, preferably one or more of amino acid positions 76, 77 and 78 of SEQ ID NO: 1. In a preferred aspect, the secretion signal sequence of the invention is SEQ ID NO: 1, modified at one or more of amino acid positions 64, 65, 66, 71, 72, 73, 74, 75, 76, 77, 78, 79, 80, 82, 83, 84 and 85 of SEQ ID NO: 1, preferably at one or more of amino acid positions 76, 77 and 78 of SEQ ID NO: 1.

In yet another embodiment of the invention, the secretion signal sequence of the invention is an aMF secretion signal sequence modified by substituting or deleting one or more amino acid residues at one or more positions corresponding to one or more of position 64, 65, 66, 71, 72, 73, 74, 75, 76, 77, 78, 79, 80, 82, 83, 84 and 85 of SEQ ID NO: 1, in particular one or more amino acid modifications corresponding to one or more of amino acid modifications K76R, K76H, K76A, K76P, K76del, E77T, E77A and 76KEE/AGI in SEQ ID NO: 1. In a preferred aspect, the secretion signal sequence of the invention is SEQ ID NO: 1, modified by substituting or deleting one or more amino acid residues at one or more of position 64, 65, 66, 71, 72, 73, 74, 75, 76, 77, 78, 79, 80, 82, 83, 84 and 85 of SEQ ID NO: 1, in particular one or more amino acid modifications of K76R, K76H, K76A, K76P, K76del, E77T, E77A and 76KEE/AGI in SEQ ID NO: 1.

More specifically, the modified aMF secretion signal sequence may comprise or consist of any one of the amino acid sequences of SEQ ID NO: 2 to 9.

The present invention further relates nucleic acids encoding such secretion signal sequence as well as nucleic acids encoding a polypeptide of the invention fused to such secretion signal sequence (these are also referred to as "nucleic acid(s) of the invention"); and to host cells comprising such nucleic acids, expressing and/or processing or capable of expressing and/or processing such secretion signal sequences and/or expressing and/or processing or capable of expressing and/or processing a polypeptide of the invention fused to such secretion signal sequence.

In one embodiment, the invention relates to a nucleic acid encoding a secretion signal sequence, in particular to a nucleic acid encoding an aMF secretion signal sequence modified at one or more non-canonical cleavage sites that are present in the native aMF secretion signal sequence and that, when fused to a polypeptide of the invention and expressed and processed by a host, result in the production of N-terminal extensions of amino acid residues derived from the native aMF secretion signal sequence, as determined by mass spectrometry.

Examples of non-canonical cleavage sites that are present in the native secretion signal sequence of SEQ ID NO: 1 are non-canonical cleavage sites that, when fused to a polypeptide of the invention and expressed and processed by a host, result in the production of N-terminal extensions of 2, 3, 7, 9, 11, 12, 13, 14 or 21 amino acid residues derived from the native secretion signal sequence of SEQ ID NO: 1.

Accordingly, in another embodiment, the invention relates to a nucleic acid encoding an aMF secretion signal sequence modified at one or more non-canonical cleavage sites corresponding to the non-canonical cleavage sites that are present in the native aMF secretion signal sequence of SEQ ID NO: 1 and that, when fused to a polypeptide of the invention and expressed and processed by a host, result in the production of N-terminal extensions of 2, 3, 7, 9, 11, 12, 13, 14 or 21 amino acid residues derived from the native secretion signal sequence of SEQ ID NO: 1, as determined by mass spectrometry.

Accordingly, in yet another embodiment, the invention relates to a nucleic acid encoding an aMF secretion signal sequence modified by substituting one or more of the amino acid residues flanking the non-canonical cleavage sites corresponding to the non-canonical cleavage sites that are present in the native aMF secretion signal sequence in SEQ ID NO: 1 for another amino acid residue or by deleting one or more of the amino acid residues flanking the non-canonical cleavage sites corresponding to the non-canonical cleavage sites that are present in the native aMF secretion signal sequence in SEQ ID NO: 1.

In still another embodiment, the invention relates to a nucleic acid encoding an aMF secretion signal sequence modified at one or more amino acid positions corresponding to one or more of amino acid positions 64, 65, 66, 71, 72, 73, 74, 75, 76, 77, 78, 79, 80, 82, 83, 84 and 85 of SEQ ID NO: 1, preferably one or more of amino acid positions 76, 77 and 78 of SEQ ID NO: 1.

Examples of amino acid modifications are substitutions and deletions of amino acid residues at one or more positions corresponding to one or more of positions 64, 65, 66, 71, 72, 73, 74, 75, 76, 77, 78, 79, 80, 82, 83, 84 and 85 of SEQ ID NO: 1, in particular one or more amino acid modifications corresponding to amino acid modifications K76R, K76H, K76A, K76P, K76del, E77T, E77A and 76KEE/AGI in SEQ ID NO: 1.

In yet a further embodiment, the invention relates to a nucleic acid encoding a modified aMF secretion signal sequence, wherein the aMF secretion signal sequence that is modified comprises or consists of SEQ ID NO: 1.

In an additional embodiment, the invention relates to a nucleic acid encoding a modified aMF secretion signal sequence that comprises or consists of any one of the amino acid sequences of SEQ ID NO: 2 to 9.

In still another embodiment, the invention relates to a nucleic acid encoding a modified aMF secretion signal sequence as described above fused to a polypeptide comprising one or more immunoglobulin single variable domains.

A nucleic acid of the invention can be in the form of single or double stranded DNA or RNA, and is preferably in the form of double stranded DNA. For example, the nucleotide sequences of the invention may be genomic DNA, cDNA or synthetic DNA (such as DNA with a codon usage that has been specifically adapted for expression in the intended host cell or host organism).

According to one aspect of the invention, the nucleic acid of the invention is in essentially isolated form, as defined herein.

The nucleic acid of the invention may also be in the form of, be present in and/or be part of a vector, such as for example a plasmid, cosmid or YAC, which again may be in essentially isolated form.

The nucleic acids of the invention can be prepared or obtained in a manner known per se, based on the information of the amino acid sequences for the polypeptides of the invention given herein. Also, as will be clear to the skilled person, to prepare a nucleic acid of the invention, also several nucleotide sequences, such as at least one nucleotide sequence encoding a Nanobody and for example nucleic acids encoding one or more linkers can be linked together in a suitable manner.

Techniques for generating the nucleic acids of the invention will be clear to the skilled person and may for instance include, but are not limited to, automated DNA synthesis; site-directed mutagenesis; combining two or more naturally occurring and/or synthetic sequences (or two or more parts thereof), introduction of mutations that lead to the expression of a truncated expression product; introduction of one or more restriction sites (e.g. to create cassettes and/or regions that may easily be digested and/or ligated using suitable restriction enzymes), and/or the introduction of mutations by means of a PCR reaction using one or more "mismatched" primers. These and other techniques will be clear to the skilled person, and reference is again made to the standard handbooks, such as Sambrook et al. and Ausubel et al., mentioned above, as well as the Examples below.

The nucleic acid of the invention may also be in the form of, be present in and/or be part of a genetic construct, as will be clear to the person skilled in the art and as described on pages 131-134 of WO 08/020,079 (incorporated herein by reference). Such genetic constructs generally comprise at least one nucleic acid of the invention that is optionally linked to one or more elements of genetic constructs known per se, such as for example one or more suitable regulatory elements (such as a suitable promoter(s), enhancer(s), terminator(s), etc.) and the further elements of genetic constructs referred to herein. Such genetic constructs comprising at least one nucleic acid of the invention will also be referred to herein as "genetic constructs of the invention".

The genetic constructs of the invention may be DNA or RNA, and are preferably double-stranded DNA. The genetic constructs of the invention may also be in a form suitable for transformation of the intended host cell or host organism, in a form suitable for integration into the genomic DNA of the intended host cell or in a form suitable for independent replication, maintenance and/or inheritance in the intended host organism. For instance, the genetic constructs of the invention may be in the form of a vector, such as for example a plasmid, cosmid, YAC, a viral vector or transposon. In particular, the vector may be an expression vector, i.e. a vector that can provide for expression in vitro and/or in vivo (e.g. in a suitable host cell, host organism and/or expression system).

In one embodiment, a genetic construct of the invention comprises
i) at least one nucleic acid of the invention; operably connected to
ii) one or more regulatory elements, such as a promoter and optionally a suitable terminator; and optionally also iii) one or more further elements of genetic constructs known per se;

in which the terms "operably connected" and "operably linked" have the meaning given on pages 131-134 of WO 08/020,079; and in which the "regulatory elements", "promoter", "terminator" and "further elements" are as described on pages 131-134 of WO 08/020,079; and in which the genetic constructs may further be as described on pages 131-134 of WO 08/020,079.

The present invention also relates to a polypeptide, pharmaceutical unit dosage form or kit obtainable by or obtained by the methods of the invention as described herein. More in particular, the present invention relates to a secreted polypeptide, the secretion of which is effected by fusing the polypeptide to a secretion signal sequence, in particular a modified aMF secretion signal sequence, said polypeptide comprising one or more immunoglobulin variable domains, preferably immunoglobulin single variable domains, and an N-terminal extension of amino acid residues derived from the secretion signal sequence, said polypeptide obtainable by or obtained by:
   a) maintaining a host under conditions that are such that said host expresses and/or produces the polypeptide;
   b) isolating and/or purifying the secreted polypeptide from the medium;
wherein less than about 5% of the secreted polypeptide isolated and/or purified in step b) contains N-terminal extensions of amino acid residues derived from the secretion signal sequence, as determined by mass spectrometry.

In one aspect, the present invention relates to a secreted polypeptide, the secretion of which is effected by fusing the polypeptide to a secretion signal sequence, in particular a modified aMF secretion signal sequence, obtainable by or obtained by the methods of the invention as described herein and comprising one or more immunoglobulin variable domains, preferably immunoglobulin single variable domains, and an N-terminal extension of at least one amino acid residue derived from the secretion signal sequence.

The polypeptide obtainable by or obtained by the method of the invention as described above is characterized by a reduced level (less than about 5%, preferably less than about 3.5%, more preferably less than about 2.5%, most preferably less than about 2%), of polypeptide containing N-terminal extensions of amino acid residues derived from the secretion signal sequence. In view of the reduced level of polypeptide containing N-terminal extensions of amino acid residues derived from the secretion signal sequence, the polypeptide obtainable by or obtained by the method of the invention is advantageous as compared to prior art preparations. For example, the polypeptide of the present invention will be more homogenous and contain a higher fraction of intact polypeptides.

In a further aspect, the present invention also relates to compounds (also referred to as "compounds of the invention") obtainable by the methods of the present invention as described herein. More particularly, the present invention relates to compounds that comprise a secreted polypeptide of the invention coupled to one or more groups, residues or moieties.

Accordingly, the present invention also relates to compounds obtainable by or obtained by a method comprising the steps of:
   a) maintaining a host under conditions that are such that said host expresses and/or produces a polypeptide, the secretion of which is effected by fusing the polypeptide to a secretion signal sequence, in particular a modified aMF secretion signal sequence, said polypeptide comprising one or more (single) variable domains and an N-terminal extension of amino acid residues derived from the secretion signal sequence;

b) isolating and/or purifying the secreted polypeptide from the medium wherein less than about 5% (preferably less than about 3.5%, more preferably less than about 2.5%, most preferably less than about 2%) of the secreted polypeptide isolated and/or purified contains N-terminal extensions of amino acid residues derived from the secretion signal sequence, as determined by mass spectrometry;

c) coupling one or more groups, residues or moieties to the secreted polypeptide.

Examples of groups, residues or moieties that can be coupled to the secreted polypeptide will be know to the one skilled in the art and/or are as described herein.

The present invention also relates to pharmaceutical preparations and other compositions comprising the polypeptide and/or compound obtainable by or obtained by the methods of the present invention. The present invention also relates to the diagnostic, prophylactic and/or medical use of the polypeptides and/or compounds obtainable by or obtained by the method of the present invention.

Accordingly, the present invention also relates to a pharmaceutical unit dosage or kit obtainable or obtained by a method comprising the steps of:

a) maintaining a host under conditions that are such that said host expresses and/or produces a secreted polypeptide comprising one or more immunoglobulin variable domains, the secretion of which is effected by fusing the polypeptide to a secretion signal sequence;

b) isolating and/or purifying the secreted polypeptide from the medium wherein less than about 5% (preferably less than about 3.5%, more preferably less than about 2.5%, most preferably less than about 2%) of the secreted polypeptide isolated and/or purified contains N-terminal extensions of amino acid residues derived from the secretion signal sequence, as determined by mass spectrometry;

c) processing the obtained polypeptide into a pharmaceutical unit dosage form and/or kit.

The skilled person can readily formulate pharmaceutically suitable formulations on the basis of common general knowledge. Moreover, the references specifically dealing with (single) domain antibodies and/or Nanobodies, which are cited herein, are explicitly referred to. Without limitation, formulations for standard routes of application can be prepared, including formulations for nasal, oral, intravenous, subcutaneous, intramuscular, intraperitoneal, intravaginal, rectal application, topical application or application by inhalation.

Based on the present invention, the skilled person can also readily devise suitable methods of prevention and/or treatment characterized by the use of a therapeutically effective amount of the compound of the present invention.

Based on the present invention, the skilled person can also readily devise suitable methods of diagnosis characterized by the use of a compound of the present invention. Accordingly, the present invention also relates to diagnostic kits comprising the compound of the present invention and/or obtained by the method of the invention.

The invention will now be further described by means of the following non-limiting preferred examples and figures.

EXAMPLES

Example 1

Analysis by RP-HPLC Surprisingly Revealed the Presence of Different Pre-Peaks in Nanobody Material Produced in *Pichia Pastoris*

Production of Nanobodies in lower eukaryotic hosts such as *P. pastoris* has been extensively described in WO 94/025591 and is known to result in good quality product. Moreover, as outlined in WO 2010/125187, material produced in *P. pastoris* is characterized by equal functionality and even higher homogeneity as compared to *E. coli* produced material.

The secretion signal sequence that is most frequently used in *P. pastoris* to successfully produce a wide range of heterologous proteins is the secretion signal sequence of the prepro-alpha-factor from *Saccharomyces cerevisiae* (hereinafter also referred to as "aMF secretion signal sequence"). Ghosalkar et al. 2008 show that an aMF secretion signal sequence with only the Kex2 cleavage side (i.e. in the absence of EA repeats) secreted protein having the exact amino acid sequence as reported for the native protein.

It was therefore surprising that, when using the aMF secretion signal sequence (SEQ ID NO: 1) under different fermentation conditions for production of Nanobody material in *P. pastoris*, in the RP-HPLC chromatograms certain pre-peaks were observed in addition to the main product peak (see e.g. Table 3 and FIG. 3).

Example 2

Characterization of Product-Related Variants Associated with Pre-Peaks in the RP-HPLC Chromatograms of Nanobody Material Produced in *P. Pastoris*

Characterization of the product-related variants associated with the observed pre-peaks by LC-MS analysis, showed that the pre-peaks correspond to Nanobodies with different lengths of incompletely processed aMF secretion signal sequence (see Table 1), the most prominent one being the EEGVSLEKR sequence.

The presence of Nanobodies with different lengths of incompletely processed aMF secretion signal sequence, suggested the presence of different non-canonical cleavage sites in the secretion signal sequence attached to the Nanobodies.

TABLE 1

Overview of different N-terminal amino acid sequences derived from incompletely processed aMF secretion signal sequences, observed when different Nanobodies(abbreviated as Nb) were produced in Pichia pastoris strain X33.

| | Nanobody sequence | N-terminal amino acid sequence |
|---|---|---|
| Nb A | DVQLVESGGGLVQAGGSLSISCAASGGSLSNYVLGWFRQAPGKEREFV AAINWRGDITIGPPNVEGRFTISRDNAKNTGYLQMNSLAPDDTAVYYC GAGTPLNPGAYIYDWSYDYWGRGTQVTVSSGGGGSGGGGSGGGGSE VQLVESGGGLVQAGGSLSISCAASGGSLSNYVLGWFRQAPGKEREFVA AINWRGDITIGPPNVEGRFTISRDNAKNTGYLQMNSLAPDDTAVYYCG AGTPLNPGAYIYDWSYDYWGRGTQVTVSSGGGGSGGGGSGGGGSEV | EEGVSLEKR (SEQ ID NO: 56) |

TABLE 1-continued

Overview of different N-terminal amino acid sequences derived from incompletely processed aMF secretion signal sequences, observed when different Nanobodies (abbreviated as Nb) were produced in Pichia pastoris strain X33.

| Nanobody sequence | N-terminal amino acid sequence |
|---|---|
| QLVESGGGLVQAGGSLSISCAASGGSLSNYVLGWFRQAPGKEREFVAAI<br>NWRGDITIGPPNVEGRFTISRDNAKNTGYLQMNSLAPDDTAVYYCGA<br>GTPLNPGAYIYDWSYDWGRGTQVTVSS<br>(SEQ ID NO: 47) | |
| Nb B  EVQLLESGGGLVQPGGSLRLSCAASGRIFSLPASGNIFNLLTIAWYRQAP<br>GKGRELVATINSGSRTYYADSVKGRFTISRDNSKKTLYLQMNSLRPEDTA<br>VYYCQTSGSGSPNFWGQGTLVTVSSGGGGSGGGSEVQLVESGGGLVQ<br>PGNSLRLSCAASGFTFSSFGMSWVRQAPGKGLEWVSSISGSGSDTLYA<br>DSVKGRFTISRDNAKTTLYLQMNSLRPEDTAVYYCTIGGSLSRSSQGTLV<br>TVSSGGGGSGGGSEVQLLESGGGLVQPGGSLRLSCAASGRTLSSYAMG<br>WFRQAPGKGREFVARISQGGTAIYYADSVKGRFTISRDNSKNTLYLQM<br>NSLRPEDTAVYYCAKDPSPYYRGSAYLLSGSYDSWGQGTLVTVSS<br>(SEQ ID NO: 48) | None |
| Nb C  EVQLLESGGGLVQPGGSLRLSCAASGGSLSNYVLGWFRQAPGKGREFV<br>AAINWRDDITIGPPNVEGRFTISRDNSKNTLYLQMNSLRPEDTAVYYCG<br>AGTPLNPGAYIYDWSYDWGQGTLVTVSSGGGGSGGGGSGGGGSEV<br>QLLESGGGLVQPGGSLRLSCAASGGSLSNYVLGWFRQAPGKGREFVAA<br>INWRDDITIGPPNVEGRFTISRDNSKNTLYLQMNSLRPEDTAVYYCGAG<br>TPLNPGAYIYDWSYDWGQGTLVTVSS<br>(SEQ ID NO: 49) | AKEEGVSLEKR<br>(SEQ ID NO: 57)<br>AAKEEGVSLEKR<br>(SEQ ID NO: 58)<br>IAAKEEGVSLEKR<br>(SEQ ID NO: 59)<br>SIAAKEEGVSLEKR<br>(SEQ ID NO: 60) |
| Nb D  EVQLVESGGGLVQPGGSLRLSCAASGFTFSSYAMSWVRQAPGKGLEW<br>VSGIKSSGDSTRYAGSVKGRFTISRDNAKNTLYLQMNSLRPEDTAVYYC<br>AKSRVSRTGLYTYDNRGQGTLVTVSSGGGGSGGGSGGGGSGGGGSE<br>VQLVESGGGLVQPGGSLRLSCAASGRTFNNYAMGWFRQAPGKEREFV<br>AAITRSGVRSGVSAIYGDSVKDRFTISRDNAKNTLYLQMNSLRPEDTAVY<br>YCAASAIGSGALRRFEYDYSGQGTLVTVSS<br>(SEQ ID NO: 50) | EEGVSLEKR<br>(SEQ ID NO: 56)<br>AKEEGVSLEKR<br>(SEQ ID NO: 57)<br>SIAAKEEGVSLEKR<br>(SEQ ID NO: 60) |
| Nb E  EVQLLESGGGLVQPGGSLRLSCAASGRTLSSYAMGWFRQAPGKGREFV<br>ARISQGGTAIYYADSVKGRFTISRDNSKNTVYLQMNSLRPEDTAVYYCA<br>KDPSPYYRGSAYLLSGSYDSWGQGTLVTVSSGGGGSGGGGSGGGGSE<br>VQLVESGGGLVQPGNSLRLSCAASGFTFSSFGMSWVRQAPGKGLEWV<br>SSISGSGSDTLYADSVKGRFTISRDNAKTTLYLQMNSLRPEDTAVYYCTIG<br>GSLSRSSQGTLVTVSSGGGGSGGGGSGGGGSEVQLLESGGGLVQPGG<br>SLRLSCAASGRIFSLPASGNIFNLLTIAWYRQAPGKGRELVATINSGSRTY<br>YADSVKGRFTISRDNSKKTVYLQMNSLRPEDTAVYYCQTSGSGSPNFW<br>GQGTLVTVSS<br>(SEQ ID NO: 51) | AKEEGVSLEKR<br>(SEQ ID NO: 57) |
| Nb F  EVQLLESGGGLVQPGGSLRLSCAASGRIFSLPASGNIFNLLTIAWYRQAP<br>GKGRELVATINSGSRTYYADSVKGRFTISRDNSKKTVYLQMNSLRPEDT<br>AVYYCQTSGSGSPNFWGQGTLVTVSSGGGGSGGGSEVQLVESGGGLV<br>QPGNSLRLSCAASGFTFSSFGMSWVRQAPGKGLEWVSSISGSGSDTLY<br>ADSVKGRFTISRDNAKTTLYLQMNSLRPEDTAVYYCTIGGSLSRSSQGTL<br>VTVSSGGGGSGGGSEVQLLESGGGLVQPGGSLRLSCAASGRTLSSYAM<br>GWFRQAPGKGREFVARISQGGTAIYYADSVKGRFTISRDNSKNTVYLQ<br>MNSLRPEDTAVYYCAKDPSPYYRGSAYLLSGSYDSWGQGTLVTVSS<br>(SEQ ID NO: 52) | KR<br>(SEQ ID NO: 61)<br>AKEEGVSLEKR<br>(SEQ ID NO: 57) |
| Nb G  EVQLVESGGGLVQPGGSLRISCAASGSIYLINYMGWYRQAPGKQRELV<br>ATLTSGGSTNYAGSVKGRFAISRDNAKNTVYLQMNSLKPEDTAVYYCNI<br>GGTLYDRRRFESWGQGTLVTVSSGGGGSGGGGSGGGGSGGGGSGGG<br>GSGGGGSGGGGSEVQLVESGGGLVQTGASLRLSCAASGRTFSNYAMG<br>WFRQAPGKERERVAAITPRAFTTYYADSVKGRFTISRDNAKNTAYLQM<br>VSLKPEDTAVYYCAAQLVGSGSNLGRQESYAYWGQGTLVTVSSGGGGS<br>GGGGSGGGGSGGGGSGGGGSGGGGSEVQLVESGGGLVQPG<br>NSLRLSCAASGFTFSSFGMSWVRQAPGKGLEWVSSISGSGSDTLYADSV<br>KGRFTISRDNAKTTLYLQMNSLRPEDTAVYYCTIGGSLSRSSQGTLVTVS<br>S<br>(SEQ ID NO: 53) | AKEEGVSLEKR<br>(SEQ ID NO: 57) |
| Nb H  EVQLVESGGGLVQAGGSLRLSCSASGATHHTNNMGWYRQAPGKEREL<br>VANIRTGGRTDYADSVKGRFTISRDIPWNSVYLQMNSLKVEDTAVYHC<br>KSDGIYLDDSSGRWADYDSWGQGTQVTVSSGGGGSGGGGSGGGGS<br>GGGGSGGGGSGGGGSGGGGSEVQLVESGGGLVQAGGSLRLSCSASG | EEGVSLEKR<br>(SEQ ID NO: 56)<br>AKEEGVSLEKR<br>(SEQ ID NO: 57) |

TABLE 1-continued

Overview of different N-terminal amino acid sequences derived
from incompletely processed aMF secretion signal sequences,
observed when different Nanobodies (abbreviated as Nb) were
produced in Pichia pastoris strain X33.

| Nanobody sequence | N-terminal amino acid sequence |
|---|---|
| ATHHTNNMGWYRQAPGKERELVANIRTGGRTDYADSVKGRFTISRDIP<br>WNSVYLQMNSLKVEDTAVYHCKSDGIYLDDSSGRWADYDSWGQGTQ<br>VTVSS<br>(SEQ ID NO: 54) | |
| Nb I EVQLVESGGGLVQAGGSLRLSCSASGATHHTNNMGWYRQAPGKEREL<br>VANIRTGGRTDYADSVKGRFTISRDIPWNSVYLQMNSLKVEDTAVYHC<br>KSDGIYLDDSSGRWADYDSWGQGTQVTVSSGGGGSGGGGSGGGGS<br>GGGGSGGGGSGGGGSGGGGSEVQLVESGGGLVQAGGSLRLSCAASG<br>FTLDDYDMSWFRQAPGKEREMISCISSSDGRPYYEDSVKGRFTVTSDN<br>AKNTVYLQMNSLKPEDTAVYYCAAGAKIFAVPGSLCSVRNAHWGQGT<br>QVTVSS<br>(SEQ ID NO: 55) | EEGVSLEKR<br>(SEQ ID NO: 56)<br>AKEEGVSLEKR<br>(SEQ ID NO: 57)<br>SIAAKEEGVSLEKR<br>(SEQ ID NO: 60)<br>FINTTIASIAAKEEGVSLEKR<br>(SEQ ID NO: 62) |

Example 3

The Amount of Incompletely Processed Product-Related Variant can be Reduced or Avoided by Using Modified aMF Secretion Signal Sequences Different modified aMF secretion signal sequences (SEQ ID NO: 2 to 9) were produced by mutating the native aMF secretion signal sequence of SEQ ID NO: 1 at the positions indicated in Table 2:

TABLE 2

Amino acid sequence of native (SEQ ID NO: 1) and modified (SEQ ID NO: 2 to 9) aMF secretion signal sequence.

| SEQ ID NO: | mutation | Amino acid sequence |
|---|---|---|
| 1 | none | MRFPSIFTAVLFAASSALAAPVNTTTEDETAQIPAEAVIGYSDLEGDFDVAVLPF<br>SNSTNNGLLFINTTIASIAAKEEGVSLEKR |
| 2 | K76R | MRFPSIFTAVLFAASSALAAPVNTTTEDETAQIPAEAVIGYSDLEGDFDVAVLPF<br>SNSTNNGLLFINTTIASIAAREEGVSLEKR |
| 3 | K76H | MRFPSIFTAVLFAASSALAAPVNTTTEDETAQIPAEAVIGYSDLEGDFDVAVLPF<br>SNSTNNGLLFINTTIASIAAHEEGVSLEKR |
| 4 | K76A | MRFPSIFTAVLFAASSALAAPVNTTTEDETAQIPAEAVIGYSDLEGDFDVAVLPF<br>SNSTNNGLLFINTTIASIAAAEEGVSLEKR |
| 5 | K76P | MRFPSIFTAVLFAASSALAAPVNTTTEDETAQIPAEAVIGYSDLEGDFDVAVLPF<br>SNSTNNGLLFINTTIASIAAPEEGVSLEKR |
| 6 | K76del | MRFPSIFTAVLFAASSALAAPVNTTTEDETAQIPAEAVIGYSDLEGDFDVAVLPF<br>SNSTNNGLLFINTTIASIAA-EEGVSLEKR |
| 7 | E77T | MRFPSIFTAVLFAASSALAAPVNTTTEDETAQIPAEAVIGYSDLEGDFDVAVLPF<br>SNSTNNGLLFINTTIASIAAKTEGVSLEKR |
| 8 | E77A | MRFPSIFTAVLFAASSALAAPVNTTTEDETAQIPAEAVIGYSDLEGDFDVAVLPF<br>SNSTNNGLLFINTTIASIAAKAEGVSLEKR |
| 9 | 76KEE/<br>AGI | MRFPSIFTAVLFAASSALAAPVNTTTEDETAQIPAEAVIGYSDLEGDFDVAVLPF<br>SNSTNNGLLFINTTIASIAAAGIGVSLEKR |

The secretion signal sequences were fused N-terminally to Nanobody A (SEQ ID NO: 47), inserted in an expression vector derived from pPICZalpha and transformed into P. pastoris strain X33.

Typically glycerol-fed batch cultivations of P. pastoris in complex medium at 30° C. and pH 5 were performed to built-up biomass and induction was initiated by continuous addition of methanol.

To evaluate potential effects on degradation and the expression level of Nanobody A produced, each cell free supernatant was, in a first step, analyzed by SDS-page analysis (FIG. 1). In a second step, each cell free supernatant was partially purified via a small chromatographic capture step and analyzed by OD280 nm measurement (Table 3).

SDS-analysis showed an effect on expression level for the modified aMF secretion signal sequences with SEQ ID NO: 7 and 9 (FIG. 1). The expression level of Nanobody A fused to the native aMF secretion signal sequence was higher than the expression level of Nanobody A fused to the modified aMF secretion signal sequences (Table 3).

To evaluate the purity of Nanobody A produced, the partially purified Nanobody from cell free supernatant was also analyzed by RP-HPLC.

RP-HPLC chromatograms generated for the *P. pastoris* produced Nanobody A material showed varying percentages of pre-peaks, main peaks and post-peaks as indicated in Table 3. The pre-peaks having a relative retention time (RRT=Rtpeak impurity/Rtmain peak; Rt=retention time) of 0.92 or less were integrated together and pre-peaks having a RRT of more than 0.92 up to and including 0.94 were integrated together (too badly resolved to integrate as separate peaks). The respective relative area % of the pre-peaks is indicated in Table 3.

Further characterization of the peaks by LC-MS analysis, showed that:
- pre-peaks with a RRT of 0.92 or less correspond to degradation products of Nanobody A,
- pre-peaks with a RRT of more than 0.92 up to 0.94 correspond to degradation products of Nanobody A (indicated as (1) in Table 3)
- pre-peaks with a RRT of 0.94 correspond to Nanobody A with incompletely processed secretion signal sequences (indicated as (2) in Table 3),
- the main peak corresponds to intact Nanobody A, and
- the post-peaks correspond to pyroglutamate variants of Nanobody A and Nanobody A with missing disulfide bridges (as described in WO 2010/125187 and WO 2010/139808).

TABLE 4

| SEQ ID NO: | Corresponding sequence in De Schutter et al. | Amino acid sequence |
|---|---|---|
| 10 | Pipas_FragB_0067 | MLSLTKLFIGIILGAFVAA |
| 11 | Pipas_chr1-1_0011 | MRIVRSVAIAIACHCITALA |
| 12 | Pipas_chr1-1_0109 | MKLQLFTLTLSLMASSTLA |
| 13 | Pipas_chr1-1_0147 | MWILWLLTTVSA |
| 14 | Pipas_chr1-1_0160 | MKILSALLLLFTLAFA |
| 15 | Pipas_chr1-1_0293 | MRPVLSLLLLLASSVLA |
| 16 | Pipas_chr1-1_0379 | MFVIQLAFLCLGVSLTTA |
| 17 | Pipas_chr1-3_0226 | MFKSLCMLIGSCLLSSVLA |
| 18 | Pipas_chr1-3_0227 | MLSILSALTLLGLSCA |
| 19 | Pipas_chr1-3_0229 | MQVKSIVNLLLACSLAVA |
| 20 | Pipas_chr1-4_0013 | MILHTYIILSLLTIFPKAIG |
| 21 | Pipas_chr1-4_0164 | MRLLHISLLSIISVLTKANA |
| 22 | Pipas_chr1-4_0242 | MWRPLVLVLALLRVLSPAKG |
| 23 | Pipas_chr1-4_0426 | MIFNLKTLAAVAISISQVSA |
| 24 | Pipas_chr1-4_0611 | MKYLPLVATLASSALA |

TABLE 3

| SEQ ID NO: | Mutation | Expression level (g/L) | % pre-peaks with RRT of 0.92 or less | % pre-peaks with RRT of more than 0.92 up to and including 0.94 | % main peak | % post-peaks | Number of redundant amino acids at the N-terminus of incompletely processed products [2] |
|---|---|---|---|---|---|---|---|
| 1 | None | 3.78 | 2.3 | 4.7 [2] | 91.5 | 1.4 | 7, 9 |
| 2 | K76R | 2.25 | 2.3 | <3.5 [1+2] | 93.2 | 1.1 | 3, 7, 9, 11, 14 |
| 3 | K76H | 3.60 | 2.1 | <3.3 [1+2] | 93.3 | 1.2 | 7 |
| 4 | K76A | 2.70 | 0.7 | 2.2 [NA] | 96.1 | 1.0 | NA |
| 5 | K76P | 2.55 | 2.0 | 1.9 [2] | 94.5 | 1.5 | 7, 11, 14 |
| 6 | K76del | 2.40 | 2.8 | <1.6 [1+2] | 92.7 | 3.2 | 3, 11, 14 |
| 7 | E77T | 0.90 | 3.9 | 1.6 [NA] | 92.7 | 1.7 | NA |
| 8 | E77A | 2.88 | 2.4 | 3.5 [2] | 92.7 | 1.8 | 9 |
| 9 | 76KEE/AGI | 0.70 | 19.4 | 3.4 [NA] | 76.4 | 0 | NA |

[1] contains degradation products of Nanobody A;
[2] contains Nanobody A with incompletely processed secretion signal sequences;
[1+2] contains degradation products of Nanobody A[1] and Nanobody A with incompletely processed secretion signal sequences[2].

Example 4

Production of Nanobodies in *Pichia pastoris* Using *Pichia Pastoris* Secretion Signal Sequences 37 of the 54 SignalP predicted *P. pastoris* signal peptide sequences described in De Schutter et al. 2009 (Nature Biotech 27(6): 561-566) were selected based on length. In particular, sequences having less than 32 amino acid residues were selected.

For each of these 37 sequences, the part upstream of the predicted site of signal peptidase cleavage (see Table 4) was fused N-terminally to Nanobody B (SEQ ID NO: 48), inserted in an expression vector derived from pPICZalpha and transformed into *P. pastoris* strain X33.

TABLE 4-continued

| SEQ ID NO: | Corresponding sequence in De Schutter et al. | Amino acid sequence |
|---|---|---|
| 25 | Pipas_chr2-1_0052 | MLSTILNIFILLLFIQASLQ |
| 26 | Pipas_chr2-1_0156 | MIRLLALFFARQILA |
| 27 | Pipas_chr2-1_0454 | MNLYLITLLFASLCSA |
| 28 | Pipas_chr2-2_0148 | MQFGKVLFAISALAVTALG |
| 29 | Pipas_chr3_0076 | MKLSTNLILAIAAASAVVSA |
| 30 | Pipas_chr3_0120 | MKSSWKIGLFFIAFVVELVSC |
| 31 | Pipas_chr3_0179 | MLRLLTIGSIAVSLFPASA |

TABLE 4-continued

| SEQ ID NO: | Corresponding sequence in De Schutter et al. | Amino acid sequence |
|---|---|---|
| 32 | Pipas_chr3_0184 | M LYLVTVLLFLVHVVLG |
| 33 | Pipas_chr3_0299 | MNPSSLILLALSIGYSIA |
| 34 | Pipas_chr3_0394 | MYQALLVLSLICFSSA |
| 35 | Pipas_chr3_0517 | MRFINLTITSLLALASRTTA |
| 36 | Pipas_chr3_0633 | MKSVIWSLLSLLALSQALT |
| 37 | Pipas_chr3_0866 | MLVAVALVLLLSTGYA |
| 38 | Pipas_chr3_0960 | MFWLLVLSLISQALA |
| 39 | Pipas_chr3_1003 | MKFFYFAGFISLLQLIFA |
| 40 | Pipas_chr3_1145 | MKFPVPLLFLLQLFFIIATQG |
| 41 | Pipas_chr4_0305 | MKLAALSTIALTILPVALA |
| 42 | Pipas_chr4_0342 | MLNRVLLVALSCVVFFHLVTT |
| 43 | Pipas_chr4_0545 | MNLTLIFTLISLLLGVWS |
| 44 | Pipas_chr4_0559 | MVSLTRLLITGIATALQVNA |
| 45 | Pipas_chr4_0579 | MKLLDGLTISLCISMATS |
| 46 | Pipas_chr4_0692 | MMISAFVWSSLIVGLISGLLA |

Expression levels of Nanobody B fused to the above *P. pastoris* sequences or to the aMF secretion signal sequence were compared for *P. pastoris* transformants with the same copy number (evaluated by qPCR) by SDS page-analysis of small scale expressed products (5 ml culture).

Replacing the aMF secretion signal sequence with the predicted signal peptide sequences from *P. pastoris* did not increase the expression level of Nanobody B in *P. pastoris* strain X33 in shake flask experiments. The secretion signal sequences with SEQ ID NO: 17 and 38 showed the highest expression and were analysed further.

Example 5

The Formation of Incompletely Processed Product-Related Variant can be Avoided During the Production of Nanobody a by Using *Pichia Pastoris* Secretion Signal Sequences The *P. pastoris* signal peptide sequence with SEQ ID NO: 17 was fused N-terminally to Nanobody A (SEQ ID NO: 47), inserted in an expression vector derived from pPICZalpha and transformed into *P. pastoris* strain X33.

Typically glycerol-fed batch cultivations of *P. pastoris* in complex medium at 30° C. and pH 5 were performed to build-up biomass and induction was initiated by continuous addition of methanol.

To evaluate the expression level of Nanobody A produced, each cell free supernatant was evaluated via SDS-page analysis (FIG. 2) and partially purified via a small chromatographic capture step followed by OD 280 measurement. The expression level of Nanobody A fused to the aMF secretion signal sequence was higher than the expression level of Nanobody A fused to the *P. pastoris* signal peptide sequence, which might be caused by a difference in copy number. No effect on degradation could be observed.

To evaluate the purity of Nanobody A produced, the partially purified Nanobody from cell free supernatant was analyzed by RP-HPLC.

RP-HPLC chromatograms generated for the *P. pastoris* produced material showed two pre-peaks when the aMF secretion signal sequence was used (as also described in Example 3 and Table 3), which were absent when using the *P. pastoris* signal peptide sequence (FIG. 3).

The absence of degradation products of Nanobody A and Nanobody A with incompletely processed secretion signal sequences when using the *P. pastoris* signal peptide sequence was confirmed by LC-MS analysis.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein; as well as to for example the following reviews Presta 2006 (Adv. Drug Deliv. Rev. 58 (5-6): 640-56); Levin and Weiss 2006 (Mol. Biosyst. 2(1): 49-57); Irving et al. 2001 (J. Immunol. Methods 248(1-2): 31-45); Schmitz et al. 2000 (Placenta 21 Suppl. A: S106-12); Gonzales et al. 2005 (Tumour Biol. 26(1): 31-43), which describe techniques for protein engineering, such as affinity maturation and other techniques for improving the specificity and other desired properties of proteins such as immunoglobulins.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

All references disclosed herein are incorporated by reference, in particular for the teaching that is referenced hereinabove.

The invention claimed is:

1. Method for the expression and/or production of secreted polypeptides comprising one or more immunoglobulin single variable domains, the secretion of which is induced by fusing the polypeptides to a secretion signal sequence that is different from the native aMF secretion signal sequence (SEQ ID NO: 1), said method comprising the steps of:

a) maintaining a host under conditions that are such that said host expresses and/or produces the polypeptides;
b) isolating and/or purifying the secreted polypeptides from the medium;

wherein less than about 5% of the secreted polypeptides isolated and/or purified in step b) contains N-terminal extensions of amino acid residues derived from the secretion signal sequence, as determined by mass spectrometry.

2. Method according to claim 1, wherein less than about 3.5% of the polypeptides isolated and/or purified in step b) contains N-terminal extensions of amino acid residues derived from the secretion signal sequence, as determined by mass spectrometry.

3. Method according to claim 2, wherein less than about 2.5% of the polypeptides isolated and/or purified in step b) contains N-terminal extensions of amino acid residues derived from the secretion signal sequence, as determined by mass spectrometry.

4. Method according to claim 3, wherein less than about 2% of the polypeptides isolated and/or purified in step b) contains N-terminal extensions of amino acid residues derived from the secretion signal sequence, as determined by mass spectrometry.

5. Method according to claim 1, wherein the secretion of the polypeptides is induced by fusing the polypeptides to an aMF secretion signal sequence modified at one or more non-canonical cleavage sites that are present in the native aMF secretion signal sequence and that result in the production of N-terminal extensions of amino acid residues derived from the native aMF secretion signal sequence, as determined by mass spectrometry.

6. Method according to claim 5, wherein the one or more non-canonical cleavage sites correspond to the non-canonical cleavage sites that are present in the native aMF secretion signal sequence of SEQ ID NO: 1 and that result in the production of N-terminal extensions of 2, 3, 7, 9, 11, 12, 13, 14 or 21 amino acid residues derived from the native aMF secretion signal sequence of SEQ ID NO: 1.

7. Method according to claim 5, wherein the aMF secretion signal sequence is modified by substituting one or more amino acid residues flanking the non-canonical cleavage sites corresponding to the non-canonical cleavage sites that are present in the native aMF secretion signal sequence of SEQ ID NO: 1 for another amino acid residue, or by deleting one or more amino acid residues flanking the non-canonical cleavage sites corresponding to the non-canonical cleavage sites that are present in the native aMF secretion signal sequence of SEQ ID NO: 1.

8. Method according to claim 5, wherein the aMF secretion signal sequence is modified at one or more amino acid positions corresponding to one or more of amino acid positions 64, 65, 66, 71, 72, 73, 74, 75, 76, 77, 78, 79, 80, 82, 83, 84 and 85 of SEQ ID NO: 1.

9. Method according to claim 8, wherein one or more amino acid residues are substituted for another amino acid residue or deleted.

10. Method according to claim 9, wherein the aMF secretion signal sequence is modified by one or more of the following amino acid modifications: K76R, K76H, K76A, K76P, K76del, E77T, E77A and 76KEE/AGI.

11. Method according to claim 5, wherein the aMF secretion signal sequence that is modified comprises or consists of SEQ ID NO: 1.

12. Method according to claim 5, wherein the modified aMF secretion signal sequence comprises or consists of any one of the amino acid sequences of SEQ ID NO: 2 to 9.

13. Method according to claim 1, wherein the secretion of the polypeptides is induced by fusing the polypeptides to a secretion signal sequence from *Pichia pastoris*.

14. Method according to claim 13, wherein the *Pichia pastoris* secretion signal sequence comprises or consists of any one of the amino acid sequences of SEQ ID NO: 10 to 46.

15. Method according to claim 1, wherein said host is selected from prokaryotic hosts or eukaryotic hosts.

16. Method according to claim 15, wherein said eukaryotic host is selected from insect cells, mammalian cells, and lower eukaryotic hosts comprising yeasts.

17. Method according to claim 1, comprising the further step of coupling one or more groups, residues or moieties to the secreted polypeptides.

18. Method according to claim 1, comprising the further step of processing the obtained polypeptide into a pharmaceutical unit dosage form and/or kit.

19. Method according to claim 1, wherein the one or more immunoglobulin single variable domains are light chain variable domains or heavy chain variable domains.

20. Method according to claim 19, wherein the one or more immunoglobulin single variable domains are heavy chain variable domains that are derived from a conventional four-chain antibody or heavy chain variable domains that are derived from a heavy chain antibody.

21. Method according to claim 20, wherein the one or more immunoglobulin single variable domains are one or more (single) domain antibodies (or amino acid sequences that are suitable for use as a (single) domain antibody), "dAb"s (or amino acid sequences that are suitable for use as a dAb) or Nanobodies (including but not limited to a VHH sequence).

22. Method according to claim 16, wherein the yeast is selected from *Pichia, Hansenula, Saccharomyces, Kluyveromyces, Candida, Torulopsis, Torulaspora, Schizosaccharomyces, Citeromyces, Pachysolen, Debaromyces, Metschunikowia, Rhodosporidium, Leucosporidium, Botryoascus, Sporidiobolus*, and *Endomycopsis*.

* * * * *

SEQUENCE LISTING

```
<160> NUMBER OF SEQ ID NOS: 62

<210> SEQ ID NO 1
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 1

Met Arg Phe Pro Ser Ile Phe Thr Ala Val Leu Phe Ala Ala Ser Ser
```

```
                    1               5                  10                 15
Ala Leu Ala Ala Pro Val Asn Thr Thr Thr Glu Asp Glu Thr Ala Gln
                   20                  25                 30

Ile Pro Ala Glu Ala Val Ile Gly Tyr Ser Asp Leu Glu Gly Asp Phe
               35                  40                 45

Asp Val Ala Val Leu Pro Phe Ser Asn Ser Thr Asn Asn Gly Leu Leu
   50                  55                 60

Phe Ile Asn Thr Thr Ile Ala Ser Ile Ala Ala Lys Glu Glu Gly Val
65                  70                  75                 80

Ser Leu Glu Lys Arg
                85

<210> SEQ ID NO 2
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 2

Met Arg Phe Pro Ser Ile Phe Thr Ala Val Leu Phe Ala Ala Ser Ser
1               5                  10                 15

Ala Leu Ala Ala Pro Val Asn Thr Thr Thr Glu Asp Glu Thr Ala Gln
                   20                  25                 30

Ile Pro Ala Glu Ala Val Ile Gly Tyr Ser Asp Leu Glu Gly Asp Phe
               35                  40                 45

Asp Val Ala Val Leu Pro Phe Ser Asn Ser Thr Asn Asn Gly Leu Leu
   50                  55                 60

Phe Ile Asn Thr Thr Ile Ala Ser Ile Ala Ala Arg Glu Glu Gly Val
65                  70                  75                 80

Ser Leu Glu Lys Arg
                85

<210> SEQ ID NO 3
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 3

Met Arg Phe Pro Ser Ile Phe Thr Ala Val Leu Phe Ala Ala Ser Ser
1               5                  10                 15

Ala Leu Ala Ala Pro Val Asn Thr Thr Thr Glu Asp Glu Thr Ala Gln
                   20                  25                 30

Ile Pro Ala Glu Ala Val Ile Gly Tyr Ser Asp Leu Glu Gly Asp Phe
               35                  40                 45

Asp Val Ala Val Leu Pro Phe Ser Asn Ser Thr Asn Asn Gly Leu Leu
   50                  55                 60

Phe Ile Asn Thr Thr Ile Ala Ser Ile Ala Ala His Glu Glu Gly Val
65                  70                  75                 80

Ser Leu Glu Lys Arg
                85

<210> SEQ ID NO 4
<211> LENGTH: 85
<212> TYPE: PRT
<213> ORGANISM: Artificial Sequence
<220> FEATURE:
```

-continued

<223> OTHER INFORMATION: Secretion signal sequence

<400> SEQUENCE: 4

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Glu Glu Gly Val
65                  70                  75                  80

Ser Leu Glu Lys Arg
            85

<210> SEQ ID NO 5
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 5

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Pro Glu Glu Gly Val
65                  70                  75                  80

Ser Leu Glu Lys Arg
            85

<210> SEQ ID NO 6
<211> LENGTH: 84
<212> TYPE: PRT
<213> ORGANISM: Artificial Sequence
<220> FEATURE:
<223> OTHER INFORMATION: Secretion signal sequence

<400> SEQUENCE: 6

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Glu Glu Gly Val Ser
65                  70                  75                  80

Leu Glu Lys Arg

<210> SEQ ID NO 7

```
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 7

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Thr Glu Gly Val
65                  70                  75                  80

Ser Leu Glu Lys Arg
            85

<210> SEQ ID NO 8
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 8

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Ala Glu Gly Val
65                  70                  75                  80

Ser Leu Glu Lys Arg
            85

<210> SEQ ID NO 9
<211> LENGTH: 85
<212> TYPE: PRT
<213> ORGANISM: Artificial Sequence
<220> FEATURE:
<223> OTHER INFORMATION: Secretion signal sequence

<400> SEQUENCE: 9

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Ala Gly Ile Gly Val
65                  70                  75                  80
```

Ser Leu Glu Lys Arg
            85

<210> SEQ ID NO 10
<211> LENGTH: 19
<212> TYPE: PRT
<213> ORGANISM: Artificial Sequence
<220> FEATURE:
<223> OTHER INFORMATION: Secretion signal sequence

<400> SEQUENCE: 10

Met Leu Ser Leu Thr Lys Leu Phe Ile Gly Ile Ile Leu Gly Ala Phe
1               5                   10                  15

Val Ala Ala

<210> SEQ ID NO 11
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 11

Met Arg Ile Val Arg Ser Val Ala Ile Ala Ile Ala Cys His Cys Ile
1               5                   10                  15

Thr Ala Leu Ala
            20

<210> SEQ ID NO 12
<211> LENGTH: 19
<212> TYPE: PRT
<213> ORGANISM: Artificial Sequence
<220> FEATURE:
<223> OTHER INFORMATION: Secretion signal sequence

<400> SEQUENCE: 12

Met Lys Leu Gln Leu Phe Thr Leu Thr Leu Ser Leu Met Ala Ser Ser
1               5                   10                  15

Thr Leu Ala

<210> SEQ ID NO 13
<211> LENGTH: 12
<212> TYPE: PRT
<213> ORGANISM: Artificial Sequence
<220> FEATURE:
<223> OTHER INFORMATION: Secretion signal sequence

<400> SEQUENCE: 13

Met Trp Ile Leu Trp Leu Leu Thr Thr Val Ser Ala
1               5                   10

<210> SEQ ID NO 14
<211> LENGTH: 16
<212> TYPE: PRT
<213> ORGANISM: Artificial Sequence
<220> FEATURE:
<223> OTHER INFORMATION: Secretion signal sequence

<400> SEQUENCE: 14

Met Lys Ile Leu Ser Ala Leu Leu Leu Phe Thr Leu Ala Phe Ala
1               5                   10                  15

<210> SEQ ID NO 15
<211> LENGTH: 17
<212> TYPE: PRT

```
<213> ORGANISM: Artificial Sequence
<220> FEATURE:
<223> OTHER INFORMATION: Secretion signal sequence

<400> SEQUENCE: 15

Met Arg Pro Val Leu Ser Leu Leu Leu Leu Ala Ser Ser Val Leu
1               5                   10                  15

Ala

<210> SEQ ID NO 16
<211> LENGTH: 18
<212> TYPE: PRT
<213> ORGANISM: Artificial Sequence
<220> FEATURE:
<223> OTHER INFORMATION: Secretion signal sequence

<400> SEQUENCE: 16

Met Phe Val Ile Gln Leu Ala Phe Leu Cys Leu Gly Val Ser Leu Thr
1               5                   10                  15

Thr Ala

<210> SEQ ID NO 17
<211> LENGTH: 19
<212> TYPE: PRT
<213> ORGANISM: Artificial Sequence
<220> FEATURE:
<223> OTHER INFORMATION: Secretion signal sequence

<400> SEQUENCE: 17

Met Phe Lys Ser Leu Cys Met Leu Ile Gly Ser Cys Leu Leu Ser Ser
1               5                   10                  15

Val Leu Ala

<210> SEQ ID NO 18
<211> LENGTH: 16
<212> TYPE: PRT
<213> ORGANISM: Artificial Sequence
<220> FEATURE:
<223> OTHER INFORMATION: Secretion signal sequence

<400> SEQUENCE: 18

Met Leu Ser Ile Leu Ser Ala Leu Thr Leu Leu Gly Leu Ser Cys Ala
1               5                   10                  15

<210> SEQ ID NO 19
<211> LENGTH: 18
<212> TYPE: PRT
<213> ORGANISM: Artificial Sequence
<220> FEATURE:
<223> OTHER INFORMATION: Secretion signal sequence

<400> SEQUENCE: 19

Met Gln Val Lys Ser Ile Val Asn Leu Leu Leu Ala Cys Ser Leu Ala
1               5                   10                  15

Val Ala

<210> SEQ ID NO 20
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 20
```

```
Met Ile Leu His Thr Tyr Ile Ile Leu Ser Leu Leu Thr Ile Phe Pro
1               5                   10                  15

Lys Ala Ile Gly
            20
```

<210> SEQ ID NO 21
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 21

```
Met Arg Leu Leu His Ile Ser Leu Leu Ser Ile Ile Ser Val Leu Thr
1               5                   10                  15

Lys Ala Asn Ala
            20
```

<210> SEQ ID NO 22
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 22

```
Met Trp Arg Pro Leu Val Leu Val Leu Ala Leu Leu Arg Val Leu Ser
1               5                   10                  15

Pro Ala Lys Gly
            20
```

<210> SEQ ID NO 23
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 23

```
Met Ile Phe Asn Leu Lys Thr Leu Ala Ala Val Ala Ile Ser Ile Ser
1               5                   10                  15

Gln Val Ser Ala
            20
```

<210> SEQ ID NO 24
<211> LENGTH: 16
<212> TYPE: PRT
<213> ORGANISM: Artificial Sequence
<220> FEATURE:
<223> OTHER INFORMATION: Secretion signal sequence

<400> SEQUENCE: 24

```
Met Lys Tyr Leu Pro Leu Val Ala Thr Leu Ala Ser Ser Ala Leu Ala
1               5                   10                  15
```

<210> SEQ ID NO 25
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 25

```
Met Leu Ser Thr Ile Leu Asn Ile Phe Ile Leu Leu Leu Phe Ile Gln
1               5                   10                  15
```

Ala Ser Leu Gln
         20

<210> SEQ ID NO 26
<211> LENGTH: 15
<212> TYPE: PRT
<213> ORGANISM: Artificial Sequence
<220> FEATURE:
<223> OTHER INFORMATION: Secretion signal sequence

<400> SEQUENCE: 26

Met Ile Arg Leu Leu Ala Leu Phe Phe Ala Arg Gln Ile Leu Ala
1               5                   10                  15

<210> SEQ ID NO 27
<211> LENGTH: 16
<212> TYPE: PRT
<213> ORGANISM: Artificial Sequence
<220> FEATURE:
<223> OTHER INFORMATION: Secretion signal sequence

<400> SEQUENCE: 27

Met Asn Leu Tyr Leu Ile Thr Leu Leu Phe Ala Ser Leu Cys Ser Ala
1               5                   10                  15

<210> SEQ ID NO 28
<211> LENGTH: 19
<212> TYPE: PRT
<213> ORGANISM: Artificial Sequence
<220> FEATURE:
<223> OTHER INFORMATION: Secretion signal sequence

<400> SEQUENCE: 28

Met Gln Phe Gly Lys Val Leu Phe Ala Ile Ser Ala Leu Ala Val Thr
1               5                   10                  15

Ala Leu Gly

<210> SEQ ID NO 29
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 29

Met Lys Leu Ser Thr Asn Leu Ile Leu Ala Ile Ala Ala Ala Ser Ala
1               5                   10                  15

Val Val Ser Ala
         20

<210> SEQ ID NO 30
<211> LENGTH: 21
<212> TYPE: PRT
<213> ORGANISM: Artificial Sequence
<220> FEATURE:
<223> OTHER INFORMATION: Secretion signal sequence

<400> SEQUENCE: 30

Met Lys Ser Ser Trp Lys Ile Gly Leu Phe Phe Ile Ala Phe Val Val
1               5                   10                  15

Glu Leu Val Ser Cys
         20

<210> SEQ ID NO 31

```
<211> LENGTH: 19
<212> TYPE: PRT
<213> ORGANISM: Artificial Sequence
<220> FEATURE:
<223> OTHER INFORMATION: Secretion signal sequence

<400> SEQUENCE: 31

Met Leu Arg Leu Leu Thr Ile Gly Ser Ile Ala Val Ser Leu Phe Pro
1               5                   10                  15

Ala Ser Ala

<210> SEQ ID NO 32
<211> LENGTH: 17
<212> TYPE: PRT
<213> ORGANISM: Artificial Sequence
<220> FEATURE:
<223> OTHER INFORMATION: Secretion signal sequence

<400> SEQUENCE: 32

Met Leu Tyr Leu Val Thr Val Leu Leu Phe Leu Val His Val Val Leu
1               5                   10                  15

Gly

<210> SEQ ID NO 33
<211> LENGTH: 18
<212> TYPE: PRT
<213> ORGANISM: Artificial Sequence
<220> FEATURE:
<223> OTHER INFORMATION: Secretion signal sequence

<400> SEQUENCE: 33

Met Asn Pro Ser Ser Leu Ile Leu Leu Ala Leu Ser Ile Gly Tyr Ser
1               5                   10                  15

Ile Ala

<210> SEQ ID NO 34
<211> LENGTH: 16
<212> TYPE: PRT
<213> ORGANISM: Artificial Sequence
<220> FEATURE:
<223> OTHER INFORMATION: Secretion signal sequence

<400> SEQUENCE: 34

Met Tyr Gln Ala Leu Leu Val Leu Ser Leu Ile Cys Phe Ser Ser Ala
1               5                   10                  15

<210> SEQ ID NO 35
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 35

Met Arg Phe Ile Asn Leu Thr Ile Thr Ser Leu Leu Ala Leu Ala Ser
1               5                   10                  15

Arg Thr Thr Ala
            20

<210> SEQ ID NO 36
<211> LENGTH: 19
<212> TYPE: PRT
<213> ORGANISM: Artificial Sequence
<220> FEATURE:
<223> OTHER INFORMATION: Secretion signal sequence
```

-continued

<400> SEQUENCE: 36

Met Lys Ser Val Ile Trp Ser Leu Leu Ser Leu Leu Ala Leu Ser Gln
1               5                   10                  15

Ala Leu Thr

<210> SEQ ID NO 37
<211> LENGTH: 16
<212> TYPE: PRT
<213> ORGANISM: Artificial Sequence
<220> FEATURE:
<223> OTHER INFORMATION: Secretion signal sequence

<400> SEQUENCE: 37

Met Leu Val Ala Val Ala Leu Val Leu Leu Ser Thr Gly Tyr Ala
1               5                   10                  15

<210> SEQ ID NO 38
<211> LENGTH: 15
<212> TYPE: PRT
<213> ORGANISM: Artificial Sequence
<220> FEATURE:
<223> OTHER INFORMATION: Secretion signal sequence

<400> SEQUENCE: 38

Met Phe Trp Leu Leu Val Leu Ser Leu Ile Ser Gln Ala Leu Ala
1               5                   10                  15

<210> SEQ ID NO 39
<211> LENGTH: 18
<212> TYPE: PRT
<213> ORGANISM: Artificial Sequence
<220> FEATURE:
<223> OTHER INFORMATION: Secretion signal sequence

<400> SEQUENCE: 39

Met Lys Phe Phe Tyr Phe Ala Gly Phe Ile Ser Leu Leu Gln Leu Ile
1               5                   10                  15

Phe Ala

<210> SEQ ID NO 40
<211> LENGTH: 21
<212> TYPE: PRT
<213> ORGANISM: Artificial Sequence
<220> FEATURE:
<223> OTHER INFORMATION: Secretion signal sequence

<400> SEQUENCE: 40

Met Lys Phe Pro Val Pro Leu Leu Phe Leu Leu Gln Leu Phe Phe Ile
1               5                   10                  15

Ile Ala Thr Gln Gly
            20

<210> SEQ ID NO 41
<211> LENGTH: 19
<212> TYPE: PRT
<213> ORGANISM: Artificial Sequence
<220> FEATURE:
<223> OTHER INFORMATION: Secretion signal sequence

<400> SEQUENCE: 41

Met Lys Leu Ala Ala Leu Ser Thr Ile Ala Leu Thr Ile Leu Pro Val
1               5                   10                  15

Ala Leu Ala

<210> SEQ ID NO 42
<211> LENGTH: 21
<212> TYPE: PRT
<213> ORGANISM: Artificial Sequence
<220> FEATURE:
<223> OTHER INFORMATION: Secretion signal sequence

<400> SEQUENCE: 42

Met Leu Asn Arg Val Leu Leu Val Ala Leu Ser Cys Val Val Phe Phe
1               5                   10                  15

His Leu Val Thr Thr
            20

<210> SEQ ID NO 43
<211> LENGTH: 18
<212> TYPE: PRT
<213> ORGANISM: Artificial Sequence
<220> FEATURE:
<223> OTHER INFORMATION: Secretion signal sequence

<400> SEQUENCE: 43

Met Asn Leu Thr Leu Ile Phe Thr Leu Ile Ser Leu Leu Leu Gly Val
1               5                   10                  15

Trp Ser

<210> SEQ ID NO 44
<211> LENGTH: 20
<212> TYPE: PRT
<213> ORGANISM: Artificial Sequence
<220> FEATURE:
<223> OTHER INFORMATION: Secretion signal sequence

<400> SEQUENCE: 44

Met Val Ser Leu Thr Arg Leu Leu Ile Thr Gly Ile Ala Thr Ala Leu
1               5                   10                  15

Gln Val Asn Ala
            20

<210> SEQ ID NO 45
<211> LENGTH: 18
<212> TYPE: PRT
<213> ORGANISM: Artificial Sequence
<220> FEATURE:
<223> OTHER INFORMATION: Secretion signal sequence

<400> SEQUENCE: 45

Met Lys Leu Leu Asp Gly Leu Thr Ile Ser Leu Cys Ile Ser Met Ala
1               5                   10                  15

Thr Ser

<210> SEQ ID NO 46
<211> LENGTH: 21
<212> TYPE: PRT
<213> ORGANISM: Artificial Sequence
<220> FEATURE:
<223> OTHER INFORMATION: Secretion signal sequence

<400> SEQUENCE: 46

Met Met Ile Ser Ala Phe Val Trp Ser Ser Leu Ile Val Gly Leu Ile
1               5                   10                  15

Ser Gly Leu Leu Ala
            20

<210> SEQ ID NO 47
<211> LENGTH: 408
<212> TYPE: PRT
<213> ORGANISM: Artificial Sequence
<220> FEATURE:
<223> OTHER INFORMATION: Nanobody sequence

<400> SEQUENCE: 47

```
Asp Val Gln Leu Val Glu Ser Gly Gly Gly Leu Val Gln Ala Gly Gly
1               5                   10                  15

Ser Leu Ser Ile Ser Cys Ala Ala Ser Gly Gly Ser Leu Ser Asn Tyr
            20                  25                  30

Val Leu Gly Trp Phe Arg Gln Ala Pro Gly Lys Glu Arg Glu Phe Val
        35                  40                  45

Ala Ala Ile Asn Trp Arg Gly Asp Ile Thr Ile Gly Pro Pro Asn Val
    50                  55                  60

Glu Gly Arg Phe Thr Ile Ser Arg Asp Asn Ala Lys Asn Thr Gly Tyr
65                  70                  75                  80

Leu Gln Met Asn Ser Leu Ala Pro Asp Asp Thr Ala Val Tyr Tyr Cys
                85                  90                  95

Gly Ala Gly Thr Pro Leu Asn Pro Gly Ala Tyr Ile Tyr Asp Trp Ser
            100                 105                 110

Tyr Asp Tyr Trp Gly Arg Gly Thr Gln Val Thr Val Ser Ser Gly Gly
        115                 120                 125

Gly Gly Ser Gly Gly Gly Ser Gly Gly Gly Ser Glu Val Gln
    130                 135                 140

Leu Val Glu Ser Gly Gly Gly Leu Val Gln Ala Gly Ser Leu Ser
145                 150                 155                 160

Ile Ser Cys Ala Ala Ser Gly Gly Ser Leu Ser Asn Tyr Val Leu Gly
                165                 170                 175

Trp Phe Arg Gln Ala Pro Gly Lys Glu Arg Glu Phe Val Ala Ala Ile
            180                 185                 190

Asn Trp Arg Gly Asp Ile Thr Ile Gly Pro Pro Asn Val Glu Gly Arg
        195                 200                 205

Phe Thr Ile Ser Arg Asp Asn Ala Lys Asn Thr Gly Tyr Leu Gln Met
    210                 215                 220

Asn Ser Leu Ala Pro Asp Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
                245                 250                 255

Trp Gly Arg Gly Thr Gln Val Thr Val Ser Ser Gly Gly Gly Gly Ser
            260                 265                 270

Gly Gly Gly Gly Ser Gly Gly Gly Ser Glu Val Gln Leu Val Glu
        275                 280                 285

Ser Gly Gly Gly Leu Val Gln Ala Gly Ser Leu Ser Ile Ser Cys
    290                 295                 300

Ala Ala Ser Gly Gly Ser Leu Ser Asn Tyr Val Leu Gly Trp Phe Arg
305                 310                 315                 320

Gln Ala Pro Gly Lys Glu Arg Glu Phe Val Ala Ala Ile Asn Trp Arg
                325                 330                 335

Gly Asp Ile Thr Ile Gly Pro Pro Asn Val Glu Gly Arg Phe Thr Ile
            340                 345                 350

Ser Arg Asp Asn Ala Lys Asn Thr Gly Tyr Leu Gln Met Asn Ser Leu
        355                 360                 365
```

```
Ala Pro Asp Asp Thr Ala Val Tyr Tyr Cys Gly Ala Gly Thr Pro Leu
370                 375                 380

Asn Pro Gly Ala Tyr Ile Tyr Asp Trp Ser Tyr Asp Tyr Trp Gly Arg
385                 390                 395                 400

Gly Thr Gln Val Thr Val Ser Ser
                405

<210> SEQ ID NO 48
<211> LENGTH: 386
<212> TYPE: PRT
<213> ORGANISM: Artificial Sequence
<220> FEATURE:
<223> OTHER INFORMATION: Nanobody sequence

<400> SEQUENCE: 48

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

Ala Ser Gly Asn Ile Phe Asn Leu Leu Thr Ile Ala Trp Tyr Arg Gln
        35                  40                  45

Ala Pro Gly Lys Gly Arg Glu Leu Val Ala Thr Ile Asn Ser Gly Ser
    50                  55                  60

Arg Thr Tyr Tyr Ala Asp Ser Val Lys Gly Arg Phe Thr Ile Ser Arg
65                  70                  75                  80

Asp Asn Ser Lys Lys Thr Leu Tyr Leu Gln Met Asn Ser Leu Arg Pro
                85                  90                  95

Glu Asp Thr Ala Val Tyr Tyr Cys Gln Thr Ser Gly Ser Gly Ser Pro
            100                 105                 110

Asn Phe Trp Gly Gln Gly Thr Leu Val Thr Val Ser Ser Gly Gly Gly
        115                 120                 125

Gly Ser Gly Gly Gly Ser Glu Val Gln Leu Val Glu Ser Gly Gly Gly
    130                 135                 140

Leu Val Gln Pro Gly Asn Ser Leu Arg Leu Ser Cys Ala Ala Ser Gly
145                 150                 155                 160

Phe Thr Phe Ser Ser Phe Gly Met Ser Trp Val Arg Gln Ala Pro Gly
                165                 170                 175

Lys Gly Leu Glu Trp Val Ser Ser Ile Ser Gly Ser Gly Ser Asp Thr
            180                 185                 190

Leu Tyr Ala Asp Ser Val Lys Gly Arg Phe Thr Ile Ser Arg Asp Asn
        195                 200                 205

Ala Lys Thr Thr Leu Tyr Leu Gln Met Asn Ser Leu Arg Pro Glu Asp
    210                 215                 220

Thr Ala Val Tyr Tyr Cys Thr Ile Gly Gly Ser Leu Ser Arg Ser Ser
225                 230                 235                 240

Gln Gly Thr Leu Val Thr Val Ser Ser Gly Gly Gly Ser Gly Gly
                245                 250                 255

Gly Ser Glu Val Gln Leu Leu Glu Ser Gly Gly Gly Leu Val Gln Pro
            260                 265                 270

Gly Gly Ser Leu Arg Leu Ser Cys Ala Ala Ser Gly Arg Thr Leu Ser
        275                 280                 285

Ser Tyr Ala Met Gly Trp Phe Arg Gln Ala Pro Gly Lys Gly Arg Glu
    290                 295                 300

Phe Val Ala Arg Ile Ser Gln Gly Gly Thr Ala Ile Tyr Tyr Ala Asp
305                 310                 315                 320
```

```
Ser Val Lys Gly Arg Phe Thr Ile Ser Arg Asp Asn Ser Lys Asn Thr
                325                 330                 335

Leu Tyr Leu Gln Met Asn Ser Leu Arg Pro Glu Asp Thr Ala Val Tyr
            340                 345                 350

Tyr Cys Ala Lys Asp Pro Ser Pro Tyr Tyr Arg Gly Ser Ala Tyr Leu
        355                 360                 365

Leu Ser Gly Ser Tyr Asp Ser Trp Gly Gln Gly Thr Leu Val Thr Val
    370                 375                 380

Ser Ser
385

<210> SEQ ID NO 49
<211> LENGTH: 267
<212> TYPE: PRT
<213> ORGANISM: Artificial Sequence
<220> FEATURE:
<223> OTHER INFORMATION: Nanobody sequence

<400> SEQUENCE: 49

Glu Val Gln Leu Leu Glu Ser Gly Gly Gly Leu Val Gln Pro Gly Gly
1               5                   10                  15

Ser Leu Arg Leu Ser Cys Ala Ala Ser Gly Gly Ser Leu Ser Asn Tyr
            20                  25                  30

Val Leu Gly Trp Phe Arg Gln Ala Pro Gly Lys Gly Arg Glu Phe Val
        35                  40                  45

Ala Ala Ile Asn Trp Arg Asp Asp Ile Thr Ile Gly Pro Pro Asn Val
    50                  55                  60

Glu Gly Arg Phe Thr Ile Ser Arg Asp Asn Ser Lys Asn Thr Leu Tyr
65                  70                  75                  80

Leu Gln Met Asn Ser Leu Arg Pro Glu Asp Thr Ala Val Tyr Tyr Cys
            85                  90                  95

Gly Ala Gly Thr Pro Leu Asn Pro Gly Ala Tyr Ile Tyr Asp Trp Ser
        100                 105                 110

Tyr Asp Tyr Trp Gly Gln Gly Thr Leu Val Thr Val Ser Ser Gly Gly
    115                 120                 125

Gly Gly Ser Gly Gly Gly Ser Gly Gly Gly Ser Glu Val Gln
    130                 135                 140

Leu Leu Glu Ser Gly Gly Gly Leu Val Gln Pro Gly Gly Ser Leu Arg
145                 150                 155                 160

Leu Ser Cys Ala Ala Ser Gly Gly Ser Leu Ser Asn Tyr Val Leu Gly
            165                 170                 175

Trp Phe Arg Gln Ala Pro Gly Lys Gly Arg Glu Phe Val Ala Ala Ile
        180                 185                 190

Asn Trp Arg Asp Asp Ile Thr Ile Gly Pro Pro Asn Val Glu Gly Arg
    195                 200                 205

Phe Thr Ile Ser Arg Asp Asn Ser Lys Asn Thr Leu Tyr Leu Gln Met
210                 215                 220

Asn Ser Leu Arg Pro Glu Asp Thr Ala Val Tyr Tyr Cys Gly Ala Gly
225                 230                 235                 240

Thr Pro Leu Asn Pro Gly Ala Tyr Ile Tyr Asp Trp Ser Tyr Asp Tyr
            245                 250                 255

Trp Gly Gln Gly Thr Leu Val Thr Val Ser Ser
        260                 265

<210> SEQ ID NO 50
<211> LENGTH: 270
```

```
<212> TYPE: PRT
<213> ORGANISM: Artificial Sequence
<220> FEATURE:
<223> OTHER INFORMATION: Nanobody sequence

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Gly Ile Lys Ser Ser Gly Asp Ser Thr Arg Tyr Ala Gly Ser Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Pro Glu Asp Thr Ala Val Tyr Tyr Cys
                85                  90                  95

Ala Lys Ser Arg Val Ser Arg Thr Gly Leu Tyr Thr Tyr Asp Asn Arg
            100                 105                 110

Gly Gln Gly Thr Leu Val Thr Val Ser Gly Gly Gly Gly Ser Gly
            115                 120                 125

Gly Gly Gly Ser Gly Gly Gly Ser Gly Gly Gly Gly Ser Glu Val
        130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Arg Thr Phe Asn Asn Tyr Ala Met
            165                 170                 175

Gly Trp Phe Arg Gln Ala Pro Gly Lys Glu Arg Glu Phe Val Ala Ala
        180                 185                 190

Ile Thr Arg Ser Gly Val Arg Ser Gly Val Ser Ala Ile Tyr Gly Asp
    195                 200                 205

Ser Val Lys Asp Arg Phe Thr Ile Ser Arg Asp Asn Ala Lys Asn Thr
210                 215                 220

Leu Tyr Leu Gln Met Asn Ser Leu Arg Pro Glu Asp Thr Ala Val Tyr
225                 230                 235                 240

Tyr Cys Ala Ala Ser Ala Ile Gly Ser Gly Ala Leu Arg Arg Phe Glu
            245                 250                 255

Tyr Asp Tyr Ser Gly Gln Gly Thr Leu Val Thr Val Ser Ser
            260                 265                 270

<210> SEQ ID NO 51
<211> LENGTH: 398
<212> TYPE: PRT
<213> ORGANISM: Artificial Sequence
<220> FEATURE:
<223> OTHER INFORMATION: Nanobody sequence

<400> SEQUENCE: 51

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Thr Leu Ser Ser Tyr
            20                  25                  30

Ala Met Gly Trp Phe Arg Gln Ala Pro Gly Lys Gly Arg Glu Phe Val
        35                  40                  45

Ala Arg Ile Ser Gln Gly Gly Thr Ala Ile Tyr Tyr Ala Asp Ser Val
    50                  55                  60
```

Lys Gly Arg Phe Thr Ile Ser Arg Asp Asn Ser Lys Asn Thr Val Tyr
65                  70                  75                  80

Leu Gln Met Asn Ser Leu Arg Pro Glu Asp Thr Ala Val Tyr Tyr Cys
                85                  90                  95

Ala Lys Asp Pro Ser Pro Tyr Tyr Arg Gly Ser Ala Tyr Leu Leu Ser
            100                 105                 110

Gly Ser Tyr Asp Ser Trp Gly Gln Gly Thr Leu Val Thr Val Ser Ser
        115                 120                 125

Gly Gly Gly Gly Ser Gly Gly Gly Ser Gly Gly Gly Ser Glu
130                 135                 140

Val Gln Leu Val Glu Ser Gly Gly Leu Val Gln Pro Gly Asn Ser
145                 150                 155                 160

Leu Arg Leu Ser Cys Ala Ala Ser Gly Phe Thr Phe Ser Ser Phe Gly
                165                 170                 175

Met Ser Trp Val Arg Gln Ala Pro Gly Lys Gly Leu Glu Trp Val Ser
            180                 185                 190

Ser Ile Ser Gly Ser Gly Ser Asp Thr Leu Tyr Ala Asp Ser Val Lys
        195                 200                 205

Gly Arg Phe Thr Ile Ser Arg Asp Asn Ala Lys Thr Thr Leu Tyr Leu
    210                 215                 220

Gln Met Asn Ser Leu Arg Pro Glu Asp Thr Ala Val Tyr Tyr Cys Thr
225                 230                 235                 240

Ile Gly Gly Ser Leu Ser Arg Ser Ser Gln Gly Thr Leu Val Thr Val
                245                 250                 255

Ser Ser Gly Gly Gly Gly Ser Gly Gly Gly Gly Ser Gly Gly Gly Gly
            260                 265                 270

Ser Glu Val Gln Leu Leu Glu Ser Gly Gly Gly Leu Val Gln Pro Gly
        275                 280                 285

Gly Ser Leu Arg Leu Ser Cys Ala Ala Ser Gly Arg Ile Phe Ser Leu
    290                 295                 300

Pro Ala Ser Gly Asn Ile Phe Asn Leu Leu Thr Ile Ala Trp Tyr Arg
305                 310                 315                 320

Gln Ala Pro Gly Lys Gly Arg Glu Leu Val Ala Thr Ile Asn Ser Gly
                325                 330                 335

Ser Arg Thr Tyr Tyr Ala Asp Ser Val Lys Gly Arg Phe Thr Ile Ser
            340                 345                 350

Arg Asp Asn Ser Lys Lys Thr Val Tyr Leu Gln Met Asn Ser Leu Arg
        355                 360                 365

Pro Glu Asp Thr Ala Val Tyr Tyr Cys Gln Thr Ser Gly Ser Gly Ser
    370                 375                 380

Pro Asn Phe Trp Gly Gln Gly Thr Leu Val Thr Val Ser Ser
385                 390                 395

<210> SEQ ID NO 52
<211> LENGTH: 386
<212> TYPE: PRT
<213> ORGANISM: Artificial Sequence
<220> FEATURE:
<223> OTHER INFORMATION: Nanobody sequence

<400> SEQUENCE: 52

Glu Val Gln Leu Leu Glu Ser Gly Gly Gly Leu Val Gln Pro Gly Gly
1               5                   10                  15

Ser Leu Arg Leu Ser Cys Ala Ala Ser Gly Arg Ile Phe Ser Leu Pro
            20                  25                  30

```
Ala Ser Gly Asn Ile Phe Asn Leu Leu Thr Ile Ala Trp Tyr Arg Gln
         35                  40                  45
Ala Pro Gly Lys Gly Arg Glu Leu Val Ala Thr Ile Asn Ser Gly Ser
 50                  55                  60
Arg Thr Tyr Tyr Ala Asp Ser Val Lys Gly Arg Phe Thr Ile Ser Arg
 65                  70                  75                  80
Asp Asn Ser Lys Lys Thr Val Tyr Leu Gln Met Asn Ser Leu Arg Pro
                 85                  90                  95
Glu Asp Thr Ala Val Tyr Tyr Cys Gln Thr Gly Ser Gly Ser Pro
                100                 105                 110
Asn Phe Trp Gly Gln Gly Thr Leu Val Thr Val Ser Ser Gly Gly Gly
            115                 120                 125
Gly Ser Gly Gly Gly Ser Glu Val Gln Leu Val Glu Ser Gly Gly Gly
        130                 135                 140
Leu Val Gln Pro Gly Asn Ser Leu Arg Leu Ser Cys Ala Ala Ser Gly
145                 150                 155                 160
Phe Thr Phe Ser Ser Phe Gly Met Ser Trp Val Arg Gln Ala Pro Gly
                165                 170                 175
Lys Gly Leu Glu Trp Val Ser Ser Ile Ser Gly Ser Gly Ser Asp Thr
            180                 185                 190
Leu Tyr Ala Asp Ser Val Lys Gly Arg Phe Thr Ile Ser Arg Asp Asn
        195                 200                 205
Ala Lys Thr Thr Leu Tyr Leu Gln Met Asn Ser Leu Arg Pro Glu Asp
210                 215                 220
Thr Ala Val Tyr Tyr Cys Thr Ile Gly Gly Ser Leu Ser Arg Ser Ser
225                 230                 235                 240
Gln Gly Thr Leu Val Thr Val Ser Ser Gly Gly Gly Ser Gly Gly
                245                 250                 255
Gly Ser Glu Val Gln Leu Leu Glu Ser Gly Gly Gly Leu Val Gln Pro
        260                 265                 270
Gly Gly Ser Leu Arg Leu Ser Cys Ala Ala Ser Gly Arg Thr Leu Ser
            275                 280                 285
Ser Tyr Ala Met Gly Trp Phe Arg Gln Ala Pro Gly Lys Gly Arg Glu
        290                 295                 300
Phe Val Ala Arg Ile Ser Gln Gly Gly Thr Ala Ile Tyr Tyr Ala Asp
305                 310                 315                 320
Ser Val Lys Gly Arg Phe Thr Ile Ser Arg Asp Asn Ser Lys Asn Thr
                325                 330                 335
Val Tyr Leu Gln Met Asn Ser Leu Arg Pro Glu Asp Thr Ala Val Tyr
            340                 345                 350
Tyr Cys Ala Lys Asp Pro Ser Pro Tyr Tyr Arg Gly Ser Ala Tyr Leu
        355                 360                 365
Leu Ser Gly Ser Tyr Asp Ser Trp Gly Gln Gly Thr Leu Val Thr Val
        370                 375                 380
Ser Ser
385

<210> SEQ ID NO 53
<211> LENGTH: 431
<212> TYPE: PRT
<213> ORGANISM: Artificial Sequence
<220> FEATURE:
<223> OTHER INFORMATION: Nanobody sequence

<400> SEQUENCE: 53
```

```
Glu Val Gln Leu Val Glu Ser Gly Gly Gly Leu Val Gln Pro Gly Gly
1               5                   10                  15

Ser Leu Arg Ile Ser Cys Ala Ala Ser Gly Ser Ile Tyr Leu Ile Asn
            20                  25                  30

Tyr Met Gly Trp Tyr Arg Gln Ala Pro Gly Lys Gln Arg Glu Leu Val
        35                  40                  45

Ala Thr Leu Thr Ser Gly Gly Ser Thr Asn Tyr Ala Gly Ser Val Lys
    50                  55                  60

Gly Arg Phe Ala Ile Ser Arg Asp Asn Ala Lys Asn Thr Val Tyr Leu
65                  70                  75                  80

Gln Met Asn Ser Leu Lys Pro Glu Asp Thr Ala Val Tyr Tyr Cys Asn
                85                  90                  95

Ile Gly Gly Thr Leu Tyr Asp Arg Arg Arg Phe Glu Ser Trp Gly Gln
                100                 105                 110

Gly Thr Leu Val Thr Val Ser Ser Gly Gly Gly Gly Ser Gly Gly Gly
            115                 120                 125

Gly Ser Gly Gly Gly Ser Gly Gly Gly Ser Gly Gly Gly Gly
        130                 135                 140

Ser Gly Gly Gly Ser Gly Gly Gly Ser Glu Val Gln Leu Val
145                 150                 155                 160

Glu Ser Gly Gly Gly Leu Val Gln Thr Gly Ala Ser Leu Arg Leu Ser
                165                 170                 175

Cys Ala Ala Ser Gly Arg Thr Phe Ser Asn Tyr Ala Met Gly Trp Phe
            180                 185                 190

Arg Gln Ala Pro Gly Lys Glu Arg Glu Arg Val Ala Ala Ile Thr Pro
        195                 200                 205

Arg Ala Phe Thr Thr Tyr Tyr Ala Asp Ser Val Lys Gly Arg Phe Thr
    210                 215                 220

Ile Ser Arg Asp Asn Ala Lys Asn Thr Ala Tyr Leu Gln Met Val Ser
225                 230                 235                 240

Leu Lys Pro Glu Asp Thr Ala Val Tyr Tyr Cys Ala Ala Gln Leu Val
                245                 250                 255

Gly Ser Gly Ser Asn Leu Gly Arg Gln Glu Ser Tyr Ala Tyr Trp Gly
            260                 265                 270

Gln Gly Thr Leu Val Thr Val Ser Ser Gly Gly Gly Gly Ser Gly Gly
        275                 280                 285

Gly Gly Ser Gly Gly Gly Ser Gly Gly Gly Ser Gly Gly Gly
    290                 295                 300

Gly Ser Gly Gly Gly Ser Gly Gly Gly Ser Glu Val Gln Leu
305                 310                 315                 320

Val Glu Ser Gly Gly Gly Leu Val Gln Pro Gly Asn Ser Leu Arg Leu
                325                 330                 335

Ser Cys Ala Ala Ser Gly Phe Thr Phe Ser Ser Phe Gly Met Ser Trp
            340                 345                 350

Val Arg Gln Ala Pro Gly Lys Gly Leu Glu Trp Val Ser Ser Ile Ser
        355                 360                 365

Gly Ser Gly Ser Asp Thr Leu Tyr Ala Asp Ser Val Lys Gly Arg Phe
    370                 375                 380

Thr Ile Ser Arg Asp Asn Ala Lys Thr Thr Leu Tyr Leu Gln Met Asn
385                 390                 395                 400

Ser Leu Arg Pro Glu Asp Thr Ala Val Tyr Tyr Cys Thr Ile Gly Gly
                405                 410                 415
```

```
Ser Leu Ser Arg Ser Ser Gln Gly Thr Leu Val Thr Val Ser Ser
            420                 425                 430

<210> SEQ ID NO 54
<211> LENGTH: 285
<212> TYPE: PRT
<213> ORGANISM: Artificial Sequence
<220> FEATURE:
<223> OTHER INFORMATION: Nanobody sequence

<400> SEQUENCE: 54

Glu Val Gln Leu Val Glu Ser Gly Gly Gly Leu Val Gln Ala Gly Gly
1               5                  10                  15

Ser Leu Arg Leu Ser Cys Ser Ala Ser Gly Ala Thr His His Thr Asn
            20                  25                  30

Asn Met Gly Trp Tyr Arg Gln Ala Pro Gly Lys Glu Arg Glu Leu Val
        35                  40                  45

Ala Asn Ile Arg Thr Gly Gly Arg Thr Asp Tyr Ala Asp Ser Val Lys
    50                  55                  60

Gly Arg Phe Thr Ile Ser Arg Asp Ile Pro Trp Asn Ser Val Tyr Leu
65                  70                  75                  80

Gln Met Asn Ser Leu Lys Val Glu Asp Thr Ala Val Tyr His Cys Lys
                85                  90                  95

Ser Asp Gly Ile Tyr Leu Asp Asp Ser Ser Gly Arg Trp Ala Asp Tyr
            100                 105                 110

Asp Ser Trp Gly Gln Gly Thr Gln Val Thr Val Ser Ser Gly Gly Gly
        115                 120                 125

Gly Ser Gly Gly Gly Gly Ser Gly Gly Gly Gly Ser Gly Gly Gly Gly
    130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Gly Leu Val Gln Ala Gly Gly
                165                 170                 175

Ser Leu Arg Leu Ser Cys Ser Ala Ser Gly Ala Thr His His Thr Asn
            180                 185                 190

Asn Met Gly Trp Tyr Arg Gln Ala Pro Gly Lys Glu Arg Glu Leu Val
        195                 200                 205

Ala Asn Ile Arg Thr Gly Gly Arg Thr Asp Tyr Ala Asp Ser Val Lys
    210                 215                 220

Gly Arg Phe Thr Ile Ser Arg Asp Ile Pro Trp Asn Ser Val Tyr Leu
225                 230                 235                 240

Gln Met Asn Ser Leu Lys Val Glu Asp Thr Ala Val Tyr His Cys Lys
                245                 250                 255

Ser Asp Gly Ile Tyr Leu Asp Asp Ser Ser Gly Arg Trp Ala Asp Tyr
            260                 265                 270

Asp Ser Trp Gly Gln Gly Thr Gln Val Thr Val Ser Ser
        275                 280                 285

<210> SEQ ID NO 55
<211> LENGTH: 287
<212> TYPE: PRT
<213> ORGANISM: Artificial Sequence
<220> FEATURE:
<223> OTHER INFORMATION: Nanobody sequence

<400> SEQUENCE: 55

Glu Val Gln Leu Val Glu Ser Gly Gly Gly Leu Val Gln Ala Gly Gly
1               5                  10                  15
```

```
Ser Leu Arg Leu Ser Cys Ser Ala Ser Gly Ala Thr His His Thr Asn
             20                  25                  30

Asn Met Gly Trp Tyr Arg Gln Ala Pro Gly Lys Glu Arg Glu Leu Val
         35                  40                  45

Ala Asn Ile Arg Thr Gly Gly Arg Thr Asp Tyr Ala Asp Ser Val Lys
 50                  55                  60

Gly Arg Phe Thr Ile Ser Arg Asp Ile Pro Trp Asn Ser Val Tyr Leu
 65                  70                  75                  80

Gln Met Asn Ser Leu Lys Val Glu Asp Thr Ala Val Tyr His Cys Lys
                 85                  90                  95

Ser Asp Gly Ile Tyr Leu Asp Ser Ser Gly Arg Trp Ala Asp Tyr
            100                 105                 110

Asp Ser Trp Gly Gln Gly Thr Gln Val Thr Val Ser Ser Gly Gly Gly
            115                 120                 125

Gly Ser Gly Gly Gly Ser Gly Gly Gly Ser Gly Gly Gly Gly
            130                 135                 140

Ser Gly Gly Gly Gly Ser Gly Gly Gly Gly Ser Gly Gly Gly Gly Ser
145                 150                 155                 160

Glu Val Gln Leu Val Glu Ser Gly Gly Leu Val Gln Ala Gly Gly
                165                 170                 175

Ser Leu Arg Leu Ser Cys Ala Ala Ser Gly Phe Thr Leu Asp Asp Tyr
            180                 185                 190

Asp Met Ser Trp Phe Arg Gln Ala Pro Gly Lys Glu Arg Glu Met Ile
            195                 200                 205

Ser Cys Ile Ser Ser Asp Gly Arg Pro Tyr Tyr Glu Asp Ser Val
            210                 215                 220

Lys Gly Arg Phe Thr Val Thr Ser Asp Asn Ala Lys Asn Thr Val Tyr
225                 230                 235                 240

Leu Gln Met Asn Ser Leu Lys Pro Glu Asp Thr Ala Val Tyr Tyr Cys
                245                 250                 255

Ala Ala Gly Ala Lys Ile Phe Ala Val Pro Gly Ser Leu Cys Ser Val
            260                 265                 270

Arg Asn Ala His Trp Gly Gln Gly Thr Gln Val Thr Val Ser Ser
            275                 280                 285

<210> SEQ ID NO 56
<211> LENGTH: 9
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 56

Glu Glu Gly Val Ser Leu Glu Lys Arg
1               5

<210> SEQ ID NO 57
<211> LENGTH: 11
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 57

Ala Lys Glu Glu Gly Val Ser Leu Glu Lys Arg
1               5                   10
```

```
<210> SEQ ID NO 58
<211> LENGTH: 12
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 58

Ala Ala Lys Glu Glu Gly Val Ser Leu Glu Lys Arg
1               5                   10

<210> SEQ ID NO 59
<211> LENGTH: 13
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 59

Ile Ala Ala Lys Glu Glu Gly Val Ser Leu Glu Lys Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 60

Ser Ile Ala Ala Lys Glu Glu Gly Val Ser Leu Glu Lys Arg
1               5                   10

<210> SEQ ID NO 61
<211> LENGTH: 2
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 61

Lys Arg
1

<210> SEQ ID NO 62
<211> LENGTH: 21
<212> TYPE: PRT
<213> ORGANISM: Artificial Sequence
<220> FEATURE:
<223> OTHER INFORMATION: N-terminal amino acids derived from secretion
      signal sequence

<400> SEQUENCE: 62

Phe Ile Asn Thr Thr Ile Ala Ser Ile Ala Ala Lys Glu Glu Gly Val
1               5                   10                  15

Ser Leu Glu Lys Arg
            20
```